US 6,322,500 B1

(12) United States Patent
Sikora et al.

(10) Patent No.: US 6,322,500 B1
(45) Date of Patent: *Nov. 27, 2001

(54) MINIMALLY INVASIVE SURGICAL APPARATUS

(75) Inventors: George Sikora, Mansfield; Richard Beane, Hingham; Russell F. Stahl, Shrewsbury; Babs R. Soller, Northboro; Steven W. Ek, Bolton; Gary McCarthy, East Bridgewater; Bill Davis, Hingham, all of MA (US); Javier Verdura, Marrieta, GA (US)

(73) Assignee: University of Massachusetts, Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/773,485

(22) Filed: Dec. 23, 1996

(51) Int. Cl.⁷ ..................................................... A61B 1/32

(52) U.S. Cl. ..................... 600/219; 600/231; 600/232; 600/234; 600/235

(58) Field of Search ........................... 600/232, 233, 600/234, 231, 201, 228, 229, 227, 235, 205, 245, 239, 236, 237, 243

(56) References Cited

U.S. PATENT DOCUMENTS

| | | | |
|---|---|---|---|
| 1,094,575 | * | 4/1914 | Joutras ............................ 600/245 X |
| 1,839,726 | | 1/1932 | Arnold . |
| 2,070,670 | | 2/1937 | Marshall . |

(List continued on next page.)

FOREIGN PATENT DOCUMENTS

| | | | |
|---|---|---|---|
| 0 396 525 A1 | | 11/1990 | (EP) . |
| 0 791 330 | * | 8/1997 | (EP) . |
| 168216 | * | 9/1921 | (GB) ................................. 600/232 |
| 2218912 A | | 11/1989 | (GB) . |
| 2233561 | * | 1/1991 | (GB) ................................. 600/234 |
| WO 95/15715 | | 6/1995 | (WO) . |
| WO 96/05773 | | 2/1996 | (WO) . |
| 97/10753 | * | 3/1997 | (WO) . |
| WO 97/40738 | | 11/1997 | (WO) . |

OTHER PUBLICATIONS

Greenspun, Harry G. et al., "Minimally Invasive Direct Coronary Artery Bypass (MIDCAB); Surgical Techniques and Anesthetic Considerations", *Journal of Cardiothoracic and Vascular Anesthesia*, vol. 10, No. 4 (Jun. 1996) pp 507–509.

Fackler, Martin L., "Extending the Usefulness of Self–Retaining Retraction", *The American Journal of Surgery*, vol. 129 (Jun. 1975) pp. 712–715.

Brochure: "Beating Heart Bypass, A New Approach", CardioThoracic Systems, Cupertino, California 95014 ©1996.

(List continued on next page.)

*Primary Examiner*—Jeffrey A. Smith
(74) *Attorney, Agent, or Firm*—Lahive & Cockfield, LLP; David J. Rikkers, Esq.; Peter C. Lauro, Esq.

(57) ABSTRACT

The present invention encompasses tools and a tool-holding retractor assembly. The retractor assembly spreads an incision and holds the incision open. At least one extension device, having a tool holder on one end, attaches to the assembly. The holder includes a selectively locking multi-axis adjustable mounting element adapted to grip a tool shaft. The mounting element acts as a universal mounting providing rotational and sliding movement of the tool shaft. The extension device adjusts to position the tool holder peripherally of the surgical field. Once the retractor is placed, the extension device provides full access to regions below the incision. The extension device allows the surgeon to chose the insertion point and insertion angle of the tool shaft.

56 Claims, 20 Drawing Sheets

U.S. PATENT DOCUMENTS

| | | | |
|---|---|---|---|
| 2,438,646 | * 3/1948 | Pulliam | 600/231 |
| 3,522,799 | 8/1970 | Gauthier . | |
| 3,572,326 | * 3/1971 | Jensen | 600/233 |
| 3,724,449 | 4/1973 | Gauthier . | |
| 3,965,890 | 6/1976 | Gauthier . | |
| 4,010,741 | 3/1977 | Gauthier . | |
| 4,421,107 | 12/1983 | Estes et al. . | |
| 4,573,452 | * 3/1986 | Greenberg | 600/228 X |
| 4,852,552 | 8/1989 | Chaux . | |
| 4,865,019 | 9/1989 | Phillips . | |
| 4,993,862 | 2/1991 | Pelta | 403/59 |
| 5,052,374 | 10/1991 | Alvarez-Jacinto . | |
| 5,133,724 | 7/1992 | Wilson, Jr. et al. | 606/151 |
| 5,167,223 | 12/1992 | Koros et al. . | |
| 5,224,680 | 7/1993 | Greenstein et al. | 248/316 |
| 5,231,974 | 8/1993 | Giglio et al. . | |
| 5,263,956 | 11/1993 | Nobles | 606/130 |
| 5,299,563 | 4/1994 | Seton . | |
| 5,304,194 | 4/1994 | Chee et al. | 606/191 |
| 5,425,705 | 6/1995 | Evard et al. | 604/28 |
| 5,429,121 | 7/1995 | Gadelius | 600/217 |
| 5,433,700 | 7/1995 | Peters | 604/4 |
| 5,437,266 | 8/1995 | McPherson et al. | 600/217 |
| 5,452,733 | 9/1995 | Sterman et al. | 128/898 |
| 5,458,574 | 10/1995 | Machold et al. | 604/101 |
| 5,501,698 | 3/1996 | Roth et al. | 606/205 |
| 5,503,617 | 4/1996 | Jako | 600/201 |
| 5,520,610 | 5/1996 | Giglio et al. | 600/233 |
| 5,697,891 | * 12/1997 | Hori | 600/201 X |
| 5,730,757 | * 3/1998 | Benetti et al. | 606/198 |
| 5,755,660 | * 5/1998 | Tyagi | 600/232 X |
| 5,782,746 | * 7/1998 | Wright | 600/37 |
| 5,836,311 | * 11/1998 | Borst et al. | 600/201 X |
| 5,875,782 | * 3/1999 | Ferrari et al. | 600/235 X |
| 5,894,843 | * 4/1999 | Benetti et al. | 600/235 X |

OTHER PUBLICATIONS

Stevens, John H. et al., "Port–Access Coronary Artery Bypass Grafting: A Proposed Surgical Method", *J. Thorac Cardiovasc Surg* (1996) vol. 111, pp 567–573.

Schwartz, Daniel S. et al., "Minimally Invasive Cardiopulmonary Bypass with CardioPlegic Arrest: A Closed Chest Technique with Equivalent Myocardial Protection", *J. Thorac Cardiovasc Surg* (1996) vol. 111, pp 556–566.

Borst, jansen, Tulleken et al., "Coronary Artery Bypass Grafting Without Interruption of Native Coronary Flow Using a Novel Anastomosis Site Restraining Device", *J. Am Coll Cardiol* (1996) vol. 27, pp 1356–1364.

* cited by examiner

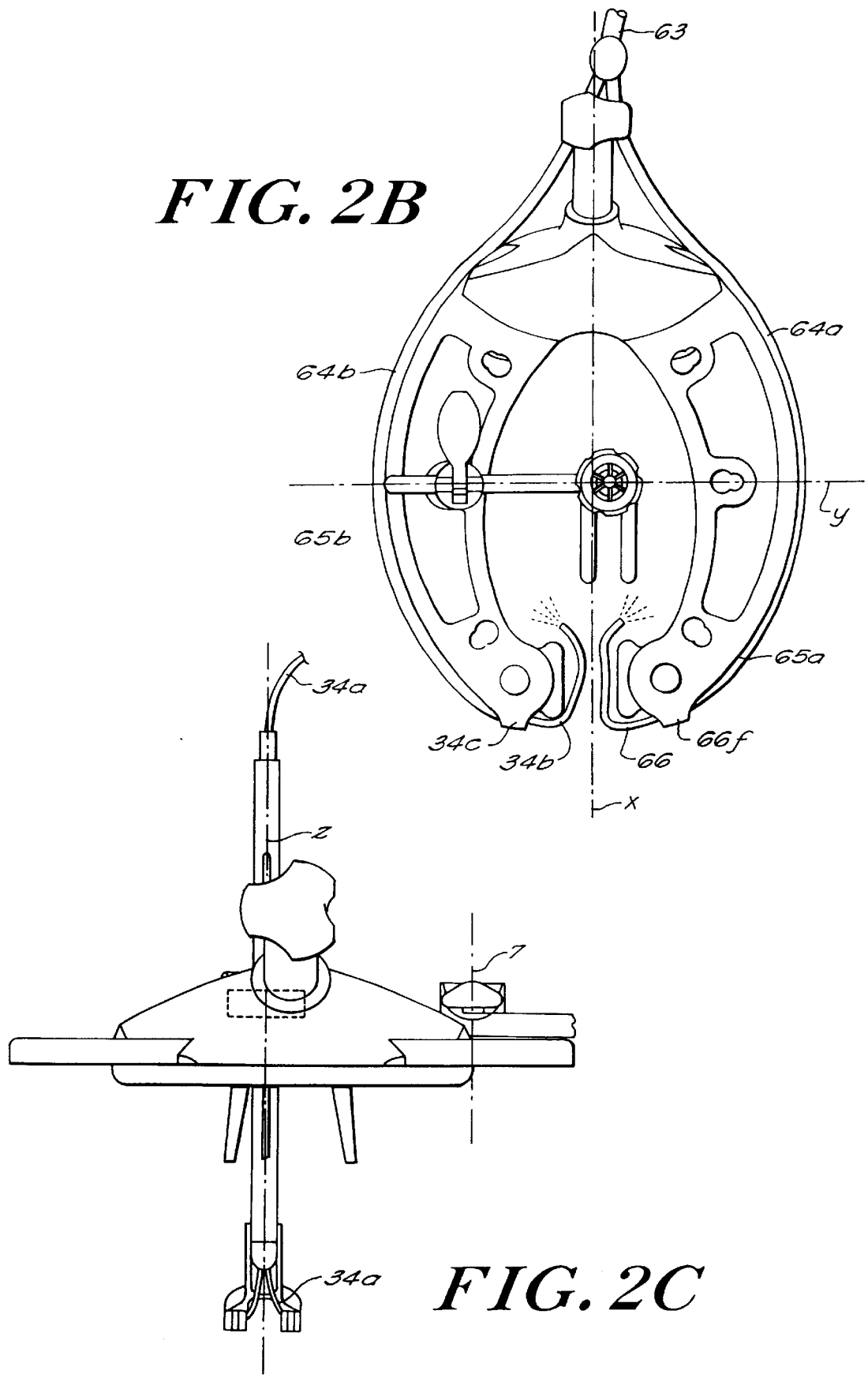

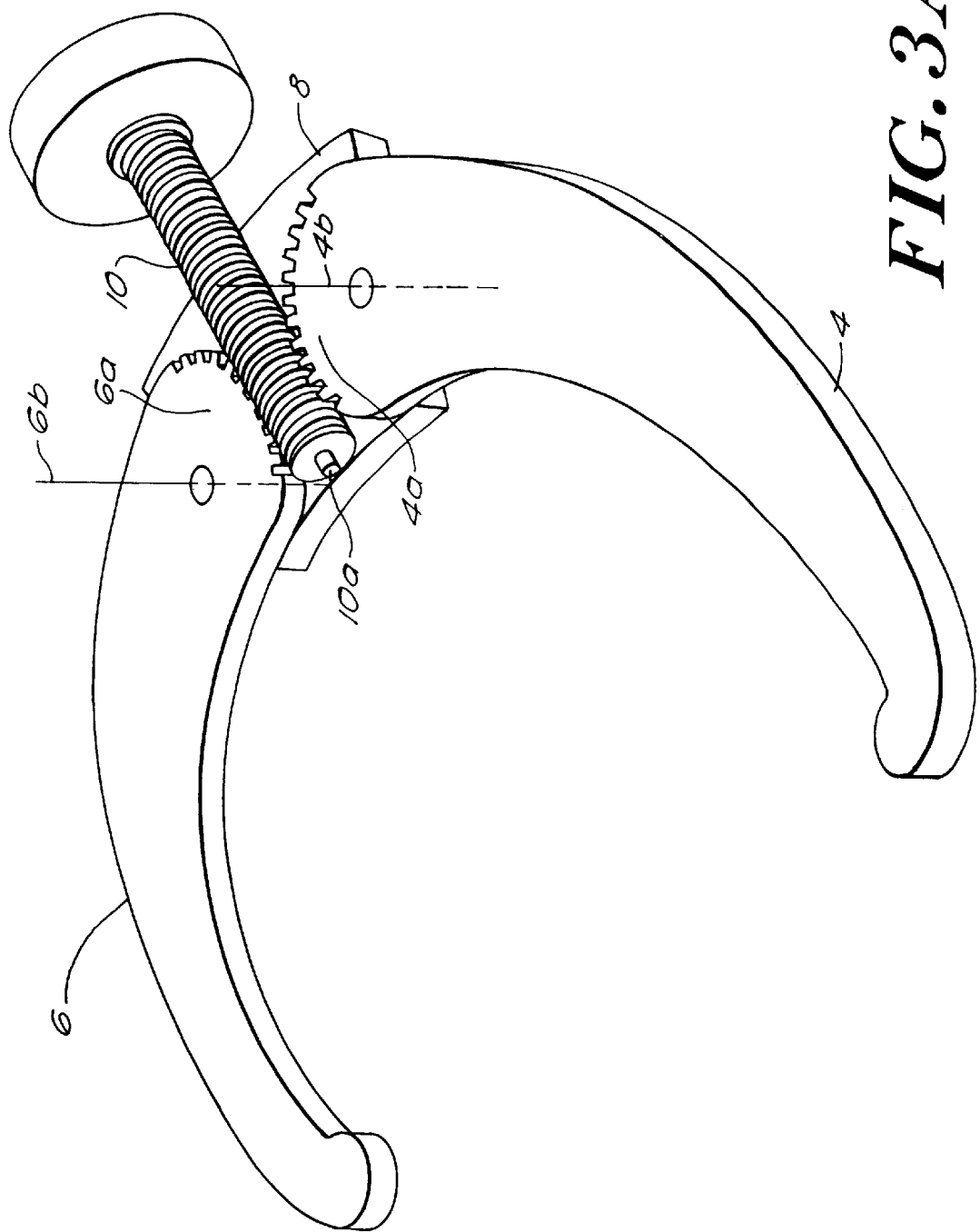

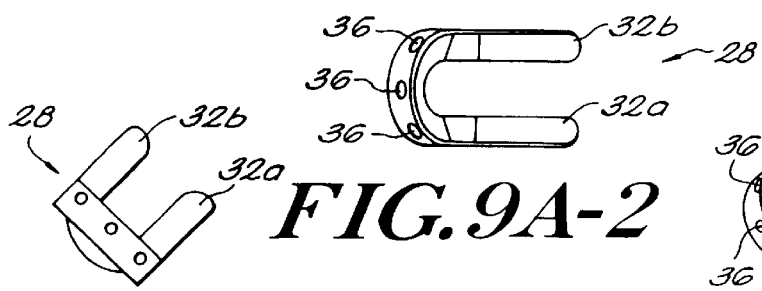
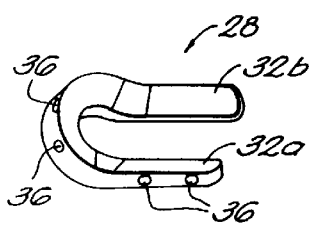
FIG.9A-1    FIG.9A-2    FIG.9A-3
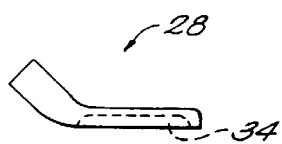
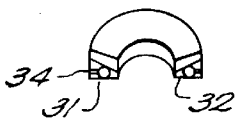
FIG.9A-4    FIG.9A-5
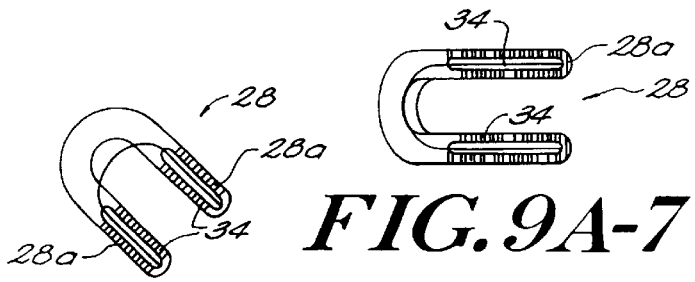
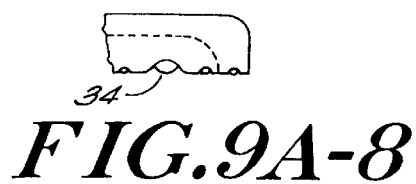
FIG.9A-6    FIG.9A-7    FIG.9A-8
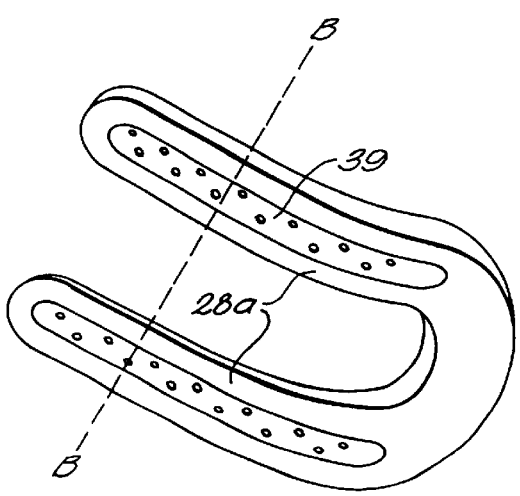
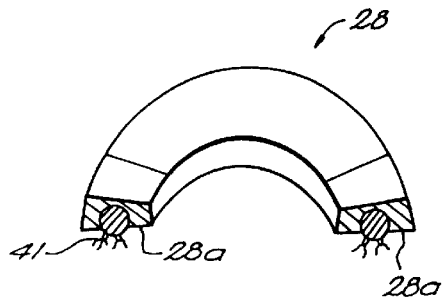
FIG.9B    FIG.9C

MINIMALLY INVASIVE SURGICAL APPARATUS

BACKGROUND

Minimally invasive or video assisted surgical procedures are being developed to reduce trauma, surgically induced complications, and costs associated with a lengthened hospital stay. One common, and costly operative procedure in the US is coronary artery bypass grafting (CABG), therefore, considerable attention has been given to establishing procedures for performing CABG surgery as a minimally invasive operation. Two basic approaches are currently being investigated by cardiac surgeons:

CABG (and other heart) operations on an arrested heart with percutaneous cardiopulmonary bypass (CPB); and CABG procedures on a beating heart without cardiopulmonary bypass.

There are certain advantages to the second approach in that CPB is known to be associated with some complications that can occur in open heart surgery. However, surgery on a beating heart is technically difficult, especially when performed through a small incision between ribs. Thus, there is a need to facilitate CABG surgery on a beating heart performed through an incision. A common CABG procedure is a graft between the left internal mammary artery (LIMA) and the left anterior descending (LAD) coronary artery. While several other coronary arteries may be treated by CABG, and other vessels can be grafted to the LAD, a LIMA-LAD graft will be discussed below as illustrative of the invention.

To access and work on the LAD while the heart is beating requires clamping or immobilizing at least a portion of the heart. Previously surgeons have used hand held surgical devices for limiting some motion of the heart. However, these devices are not particularly effective in limiting the motion of the heart and they require that an assistant place at least one hand near the surgical site. Other devices provide retractor assemblies for retracting tissue around a surgical opening to provide a sufficiently large access for surgery, and further provide mechanisms whereby retractor blades, used to pull back organs or tissue, or other surgical implements are attached to the retractor assembly. The retractor itself generally consists of a frame which fits or is assembled about a perimeter of the opening.

However, the implements of these assemblies do not have complete access to the surgical field. In other words, the mechanisms which attach the implements to the retractor assemblies allow only limited freedom of movement. Thus, if a surgeon uses such a configuration and adds further specialized surgical implements, the limited freedom of movement might complicate the surgery. For example, when a surgeon creates an incision for heart surgery and places a retractor, the heart is still covered with the pericardial membrane, an opaque tissue, and the surgeon can not clearly determine the location of the artery of interest at this point in the surgery. Thus, if the surgeon wants to attach a device to the retractor to locally limit the motion of the heart, the surgeon is required to estimate the location of the artery of interest and place the retractor and device accordingly.

Upon removing the opaque tissue and discovering the actual location of the cardiac artery, it may be necessary to reposition both the surgical implements and the retractor. To disassemble and re-configure a retractor and associated surgical implements takes time, and puts the patient at risk of complications.

Therefore, there is a need for a more versatile retractor assembly with attached surgical implements that have greater and more flexible access to the surgical field. There is also a need for surgical implements that are more effective in limiting the motion of the heart and do not require an assistant to place a hand near the surgical site.

SUMMARY OF THE PRESENT INVENTION

It is an object of this invention to provide a surgical retractor apparatus, and a related method, for holding an incision open so that a surgeon can operate on tissue under direct vision.

Another object of this invention is to provide tools and methods for use with the above retractor apparatus which will stop blood flow temporarily in selected arteries, to enable the surgeon to visualize the surgical site.

Another object of this invention is to provide tools and methods for use with the above retractor apparatus which limit the motion of a patient's heart locally, leaving the remainder of the heart to beat normally.

Another object of the invention is provide further tools and methods for use with the above retractor apparatus to assist in a surgical procedure.

The present invention encompasses novel tools and a tool-holding retractor assembly. The retractor assembly spreads an incision and holds the incision open. At least one extension device, having a tool holder on one end, attaches to the assembly. The holder includes a selectively locking multi-axis adjustable mounting element adapted to grip a tool shaft. The mounting element acts as a universal mounting providing rotational and sliding movement of the tool shaft, while the extension device adjusts to position the tool holder peripherally of the surgical field. Once the retractor is placed, the extension device provides full access to regions below the incision, so the retractor need not be re-positioned for the surgeon to position a tool at a chosen site in the surgical field. The extension device allows the surgeon to chose the insertion point and positioning angle of the tool shaft. Furthermore, the tools are designed for insertion over the edge of an incision.

BRIEF DESCRIPTION OF THE DRAWINGS

FIG. 2B is a top plan view of the retractor and extension device of FIG. 2A;

FIG. 2C is a back side view of the retractor and extension device of FIG. 2A;

FIG. 3A is a perspective view from above of an opening mechanism for the retractor of FIG. 2A;

FIG. 9A is a series of perspectives of a U-shaped end-effector;

FIG. 9B is a perspective view of a U-shaped end-effector with microtraumatic surfaces;

FIG. 9C is a cross-sectional view of the end effector of FIG. 9B viewed from a plane parallel to line B—B of FIG. 9B;

DETAILED DESCRIPTION OF THE ILLUSTRATED EMBODIMENTS

Referring to FIGS. 1–10B, one embodiment of a retractor and surgical tool attachment system according to the invention comprises a retractor 2 for spreading and keeping back the walls of an incision in a patient. In describing this embodiment, we will refer to orthogonal axes x, y, and z shown in FIGS. 2B and 2C. Much of the description of this embodiment will apply to the alternative embodiments presented below.

Figure 1:
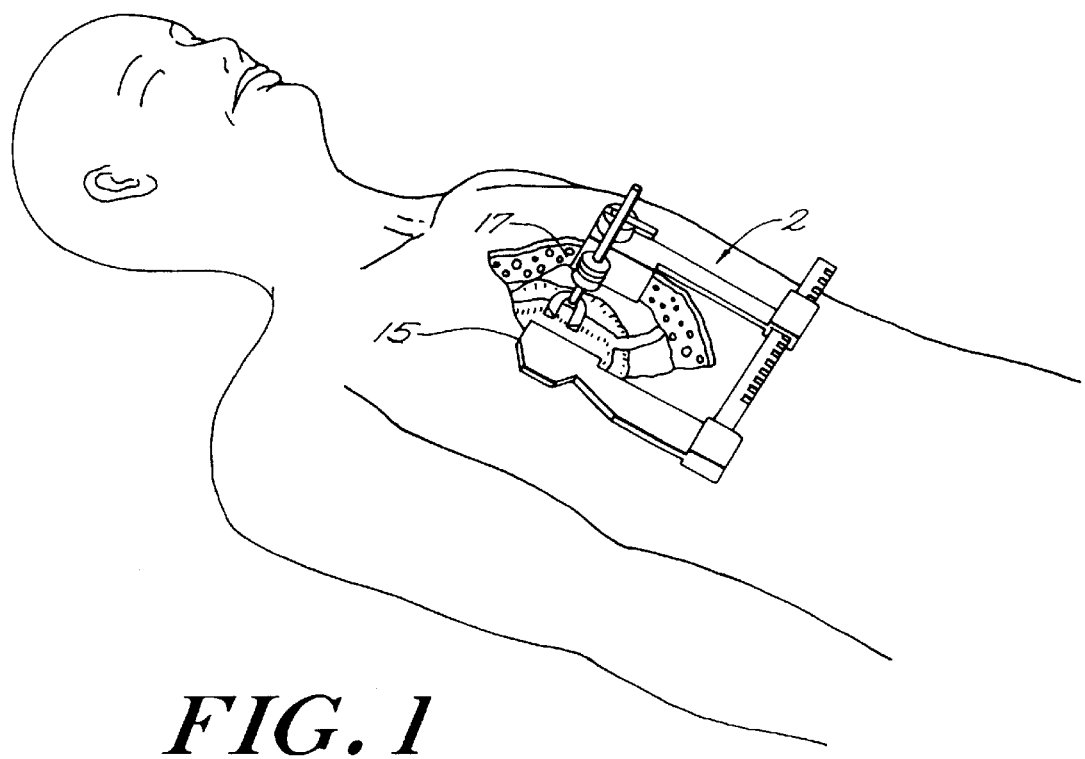
FIG. 1 is an illustration of a supine patient with a retractor according to the present invention mounted at an incision.
Figure 2A:
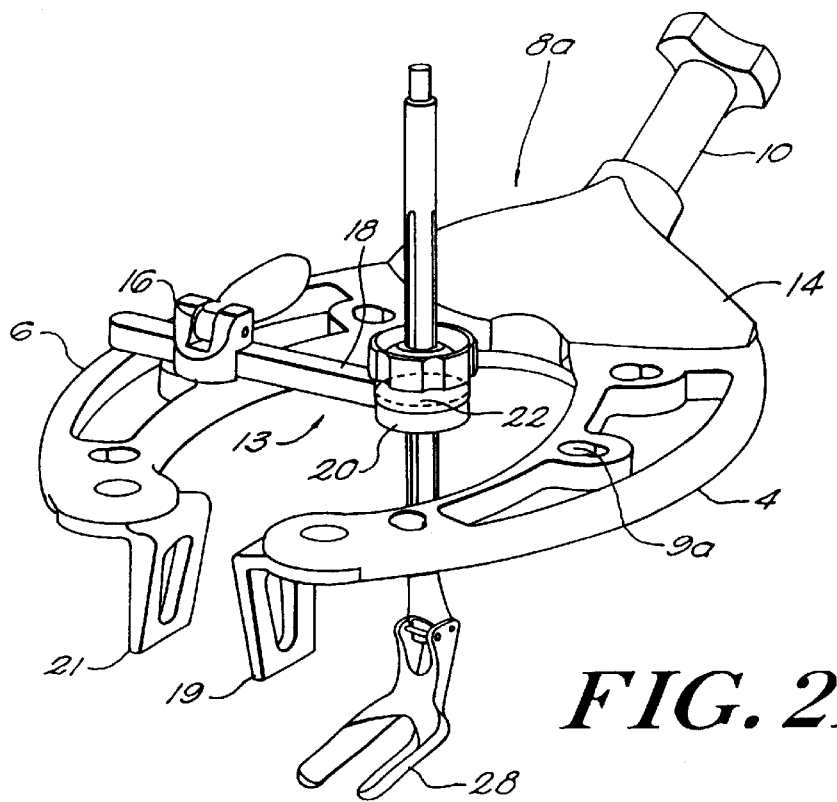
FIG. 2A is a perspective view from above of a retractor and an extension device with an attached tool, according to a preferred embodiment of the invention.
Figure 3B:
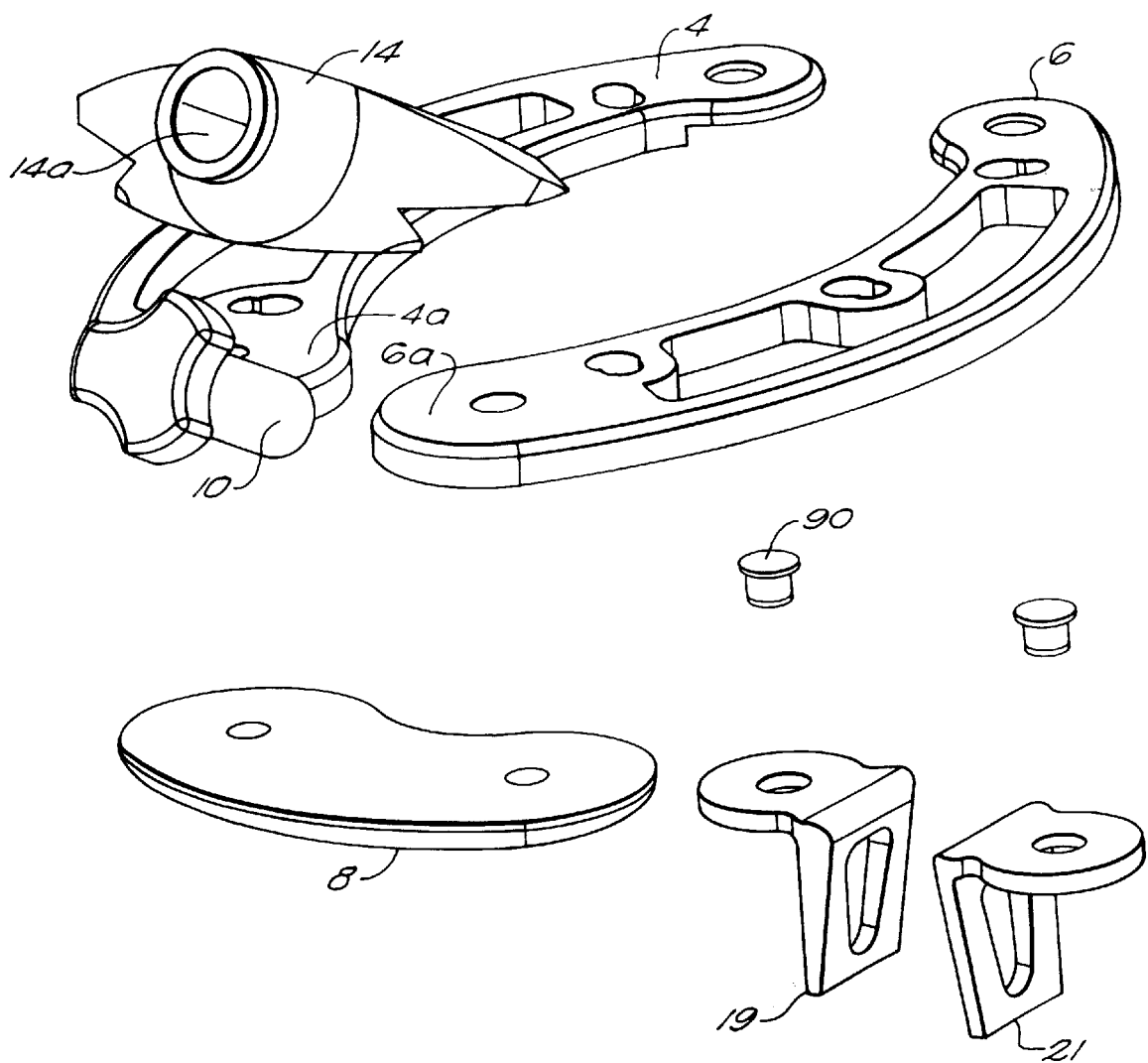
FIG. 3B is an exploded view of the opening mechanism of FIG. 3A.
Figures 1, 18A:
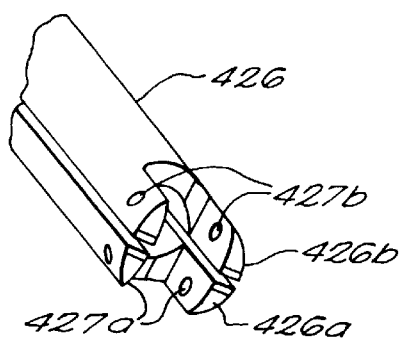
FIGS. 18A, 18B, and 18C are an exploded view from below of a tool shaft, a swivel link assembly, and a U-shaped end effector, a series of schematic illustrations of a swivel link, and a perspective view from above of an assembled swivel link, respectively.
Figures 2, 18A:
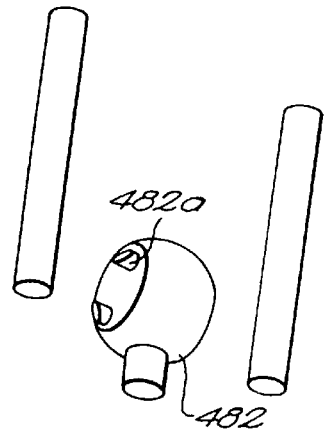
Figures 3, 18A:
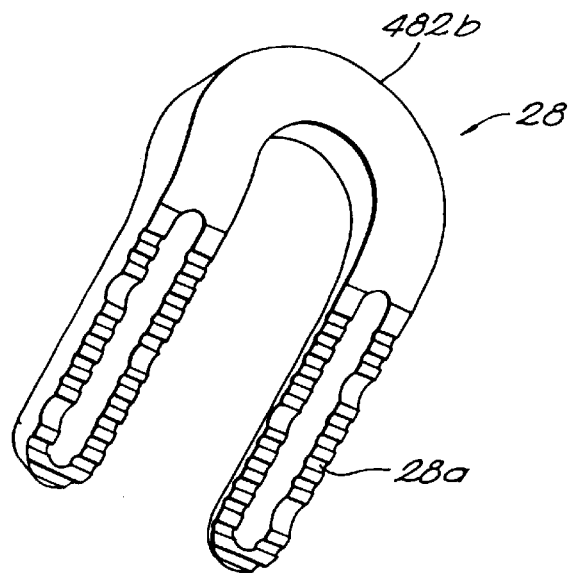
Figures 1, 18B:
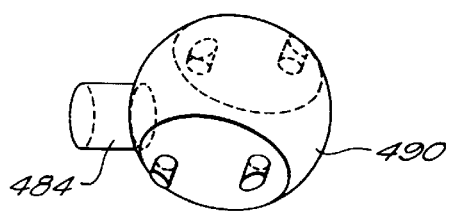
Figures 2, 18B:
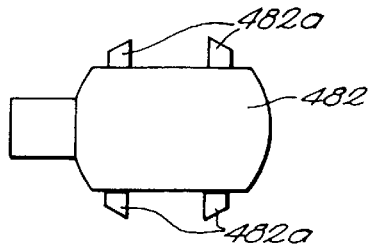
Figures 3, 18B:
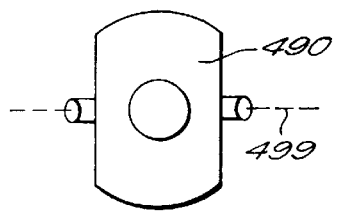
Figures 4, 18B:
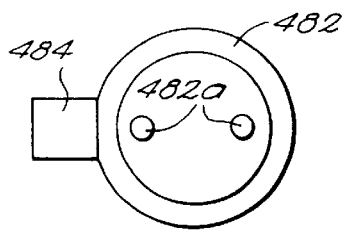
Figure 18C:
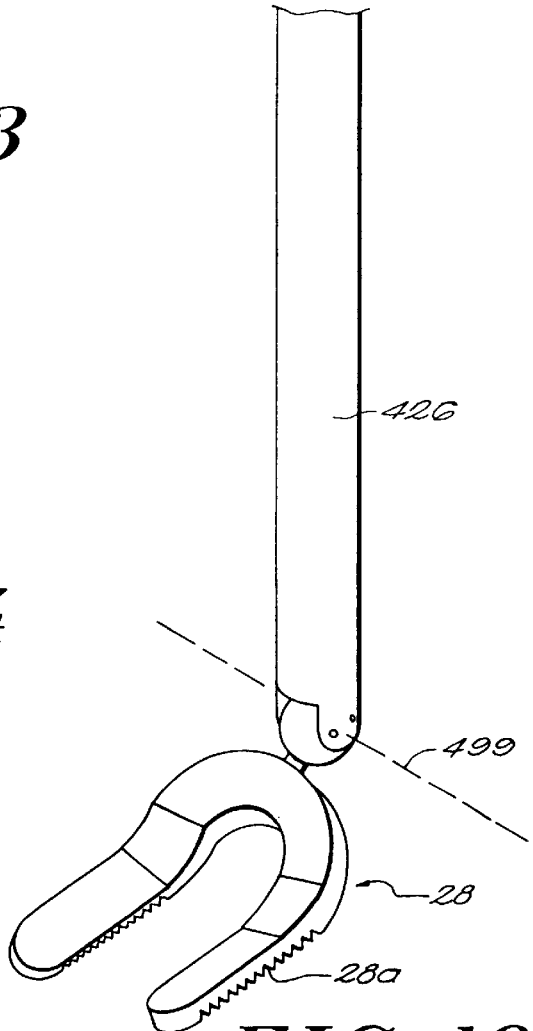

With reference to FIGS. 1–2C, the retractor includes two frame members 4 and 6, and an opening mechanism 8a. The frame members are opposed, co-extensive and generally elongated. Referring to FIGS. 2A–3B, the opening mechanism includes a connector plate 8, a screw gear 10, and a cover plate 14. The frame members 4 and 6 have proximal ends 4a and 6a with a semi-circular edge at their ends having gear teeth therein. The ends are pivotly connected to the connector plate 8 so that the frame members rotate about axes 4b and 6b, respectively. Thus, the frame members 4 and 6 move substantially in the x-y plane.

The screw gear extends between the toothed proximal ends 4a and 6a of the frame members 4 and 6 at an angle of approximately thirty degrees, forming an angled worm gear 10 assembly. The screw gear 10 turns on a guide pin 10a that is connected to the connector plate 8. A cover plate 14 sits on top of the connector plate and proximal ends 6a and 4a of the frame members 4 and 6. The cover plate 14 has a conforming angled screw slot 14a to further guide the screw.

Turning the screw 10 drives the helical worm face against the teeth of both proximal ends 4a and 4b of the frame members 4 and 6, causing the frame members 4 and 6 to pivot in opposite senses substantially in the x-y plane so the two members 4 and 6 draw toward each other, or push apart from each other, depending on the direction of rotation. This angled worm gear 10 has advantages. The angled worm gear 10 allows the gear to be self locking, i.e. the retractor can be opened to a fixed separation and it will maintain that separation. Furthermore, the angle of the worm gear 10 facilitates access to the opening mechanism by the retractor operator while maintaining access to the incision.

The frame members 4 and 6 include retractor blades 19 and 21, which extend down, transverse to the x-y plane of the frame members 4 and 6. These blades are placed in an incision when the retractor is in a closed position, i.e. when the frame members are in relative spatial proximity to each other. Upon placement of the retractor blades in an incision, the screw can be screwed down into the worm gear causing the frame members to open outwardly and the retractor blades to exert outward pressure on the walls of the incision 15 and 17, and consequently spread and keep open the incision. The frame members, the retractor blade members and the connector plate are made of a strong metal, e.g. stainless steel or titanium.

The blades 19 and 21 are modular, i.e. the blades 19 and 21 are removably and replaceably attachable to the retractor. The blades 19 and 21 can pivot about a substantially vertical axis, as shown so that they conform to the orientation of the incision, or pivot about a substantially horizontal axis. In the embodiment shown in FIGS. 2A and 2C, the blades are angled back, i.e. they tilt outwardly as they extend down, so the angle between the blade and the frame member in the y-z plane is less than 90 degrees. As the blades spread apart an incision, the pressure provided between the blades and at least a wall portion of the incision has a downward component of force, driving the retractor down against the patient's body, stabilizing the retractor. Furthermore, a blade can include a compliant blade element such as an attachable conforming elastomeric pad that attaches to the blade. Such a compliant blade element evenly distributes pressure over at least a wall portion of the incision, reducing trauma to the patient.

Figure 4:
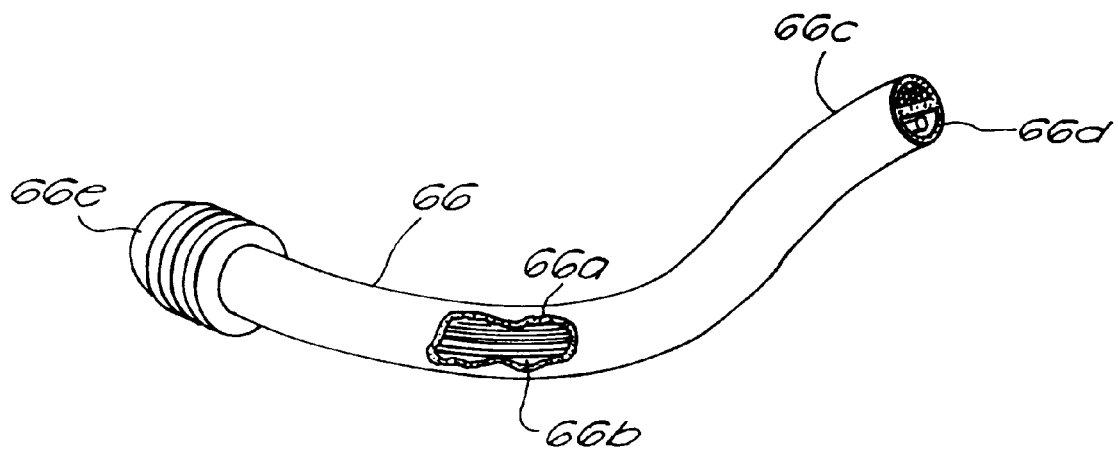
FIG. 4 is a cutaway view of a disposable light wand for use with the retractor depicted in FIG. 2B.
Figure 5:
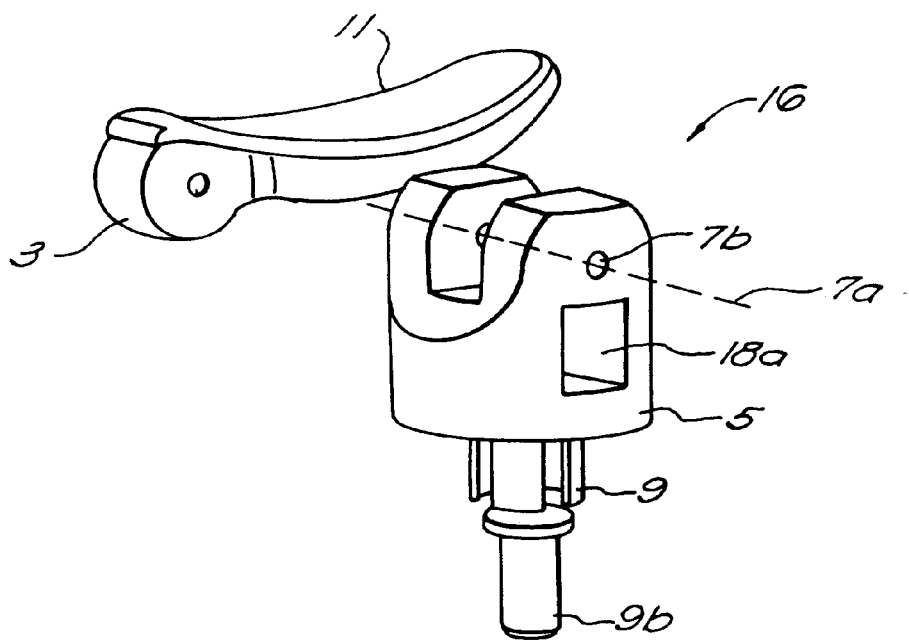
FIG. 5 is an exploded view of the cam lock clamp assembly depicted in FIGS. 2A and 2B.

With reference to FIGS. 2B and 4, the retractor of this embodiment also includes fiber optic light guide 63 optically coupled to a light source. In one embodiment, the light guide is bifurcated with each individual light guide running along light guide mounts. Individual light guide 64a travels along light guide mount 65a to a distal end of the frame member 66f, where it is optically coupled to a light wand 66, which is preferably disposable. The light wand provides light to the surgical field while its disposability facilitates sterilization of the retractor.

The disposable light wand includes a mating attachment 66e, for coupling of the light wand to the light guide, light fibers 66, full soft malleable wire 66b (316L), and dual lumen flexible tubing 66c. The tubing contains the fibers and the wire. The wire allows the tubing to be posed in any position. The end of the tubing opposite the conforming attachment has a full epoxy set at the tip. By posing the tube in an appropriate position the surgeon can illuminate an area of interest in the surgical field.

The retractor includes a suction tube 64b. This tube also contains full soft malleable wire to allow posing of the tube in any position. The proximal end of the tube is attached to a suction device. The distal end of the tube is posed in selected proximity to the surgical field. A portion of the tube near the distal end of the tube is attached to the retractor at 34c. The suction tube is used to clear blood and other material, improving visual access to the surgical field.

An extension device 13 is attachable to the frame members. The extension device attaches on top of the frame members. In one embodiment, the extension device includes a clamp assembly 16, and a positioning arm 18. The positioning arm is slideably and lockably attachable to the clamp assembly. The positioning arm has a tool holder 20 at its outboard end, that is, at the end that extends toward the incision. The tool holder includes a selectively locking multi-axis adjustable mounting element 22 adapted to grip a tool shaft 24 for positioning a tool 26. In this embodiment, the mounting element is a ball and socket joint. A cap nut with an open center tightens down to clamp the ball in the socket at the desired orientation.

Thus, by adjusting the ball and socket joint, the tool may be positioned anywhere in the surgical field. The tool 26, depicted in FIGS. 2A–2C and 6, comprises a tool shaft 24, and a end-effector 28 attached to the distal end of the tool shaft.

With reference to FIGS. 2A–2C and 5, the clamp assembly 16 for the positioning arm 18 is a cam lock, although, in other embodiments the clamp assembly could be a selectively locking second multi-axis adjustable mounting element. The cam lock includes a low cylindrical cam lock body 5, which does not project over the wall of the incision. The clamp assembly 16 attaches to the retractor by a docking means 9 that fits into a docking aperture 9a. In this embodiment, the docking means is an expanding slit cylindrical shaft with a shaft expansion pin 9b positioned inside the slit shaft and the docking aperture is a conforming cylindrical opening. The clamp assembly 16 rotates about the axis 7 of the shaft. The positioning arm 18 slideably and lockably mounts in the cylindrical body by means of a substantially rectangular conforming mounting aperture 18a. A locking lever 11 with a cam end 3 rotates about an axis 7a to drive the expansion pin into the expanding shaft while bearing down against the positioning arm to lock both the clamp assembly in a particular rotational position and the positioning arm in a particular horizontal extension position.

When the locking lever 11 is in the up or open position, the positioning arm is free to move through slot 18a and the clamp assembly 16 is free to rotate about axis 7. In addition, the clamp assembly 16 is capable of both removal and insertion in the docking aperture 9a. However, when the locking lever 11 is in the down or locked position, the cam end 3 is rotated so as to place pressure on the positioning arm 18 locking it in place. Furthermore, the cam end 3 pushes the shaft expanding pin 9b down into the cylindrical shaft 9 expanding the shaft in the conforming cylindrical slot so as to prevent rotation of the clamp assembly or removal of the clamp assembly from the docking aperture. Thus, this clamp assembly 16 allows the positioning and locking of a tool holder 20 at a fixed distance and angle with a single clamp motion.

Figure 6:
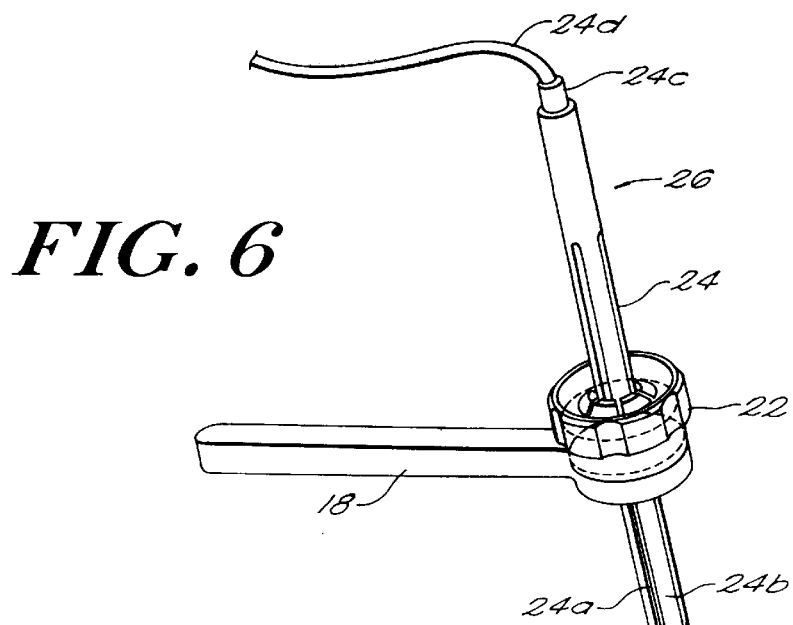
FIG. 6 is a perspective view from above of a positioning arm having a tool holder on one end and an attached tool for use with the retractor depicted in FIG. 2A.
Figure 7:
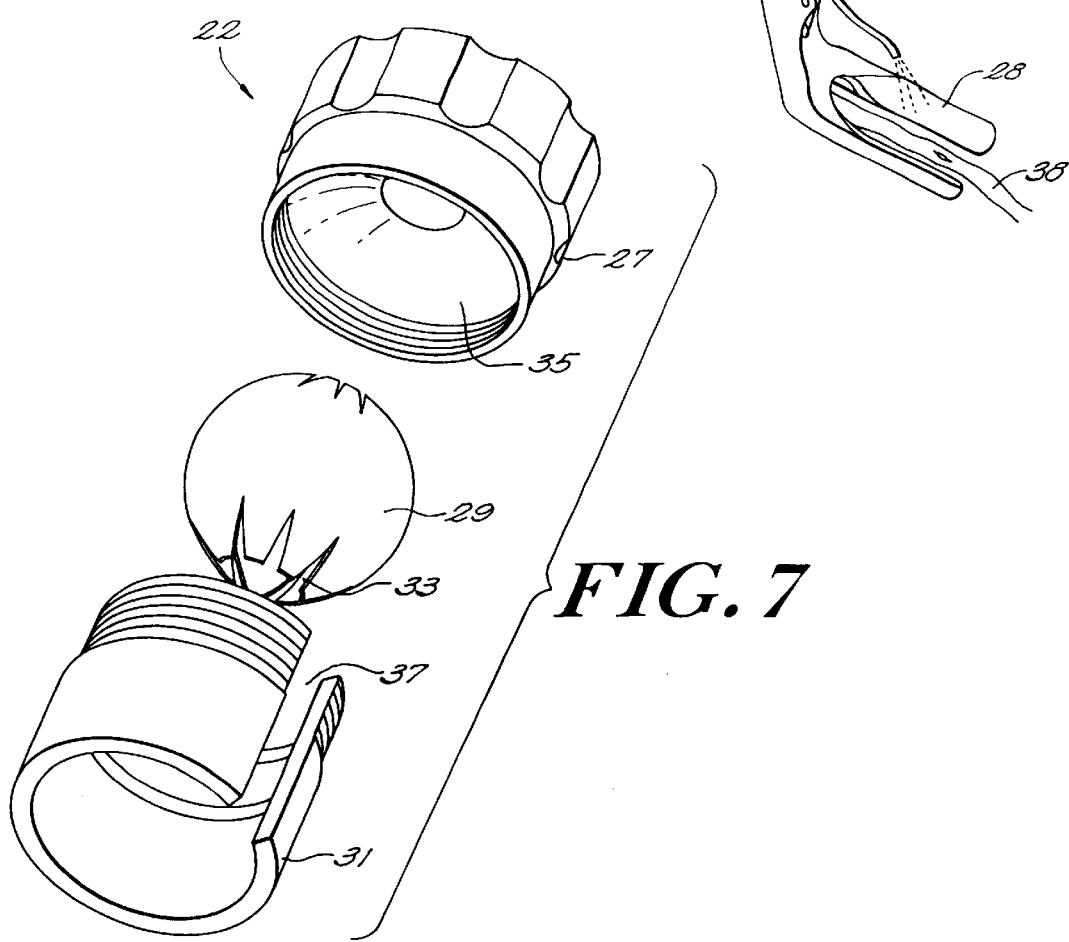
FIG. 7 is an exploded view of a ball and socket joint mounting element for use with the extension device of FIG. 2A.
Figure 8A:
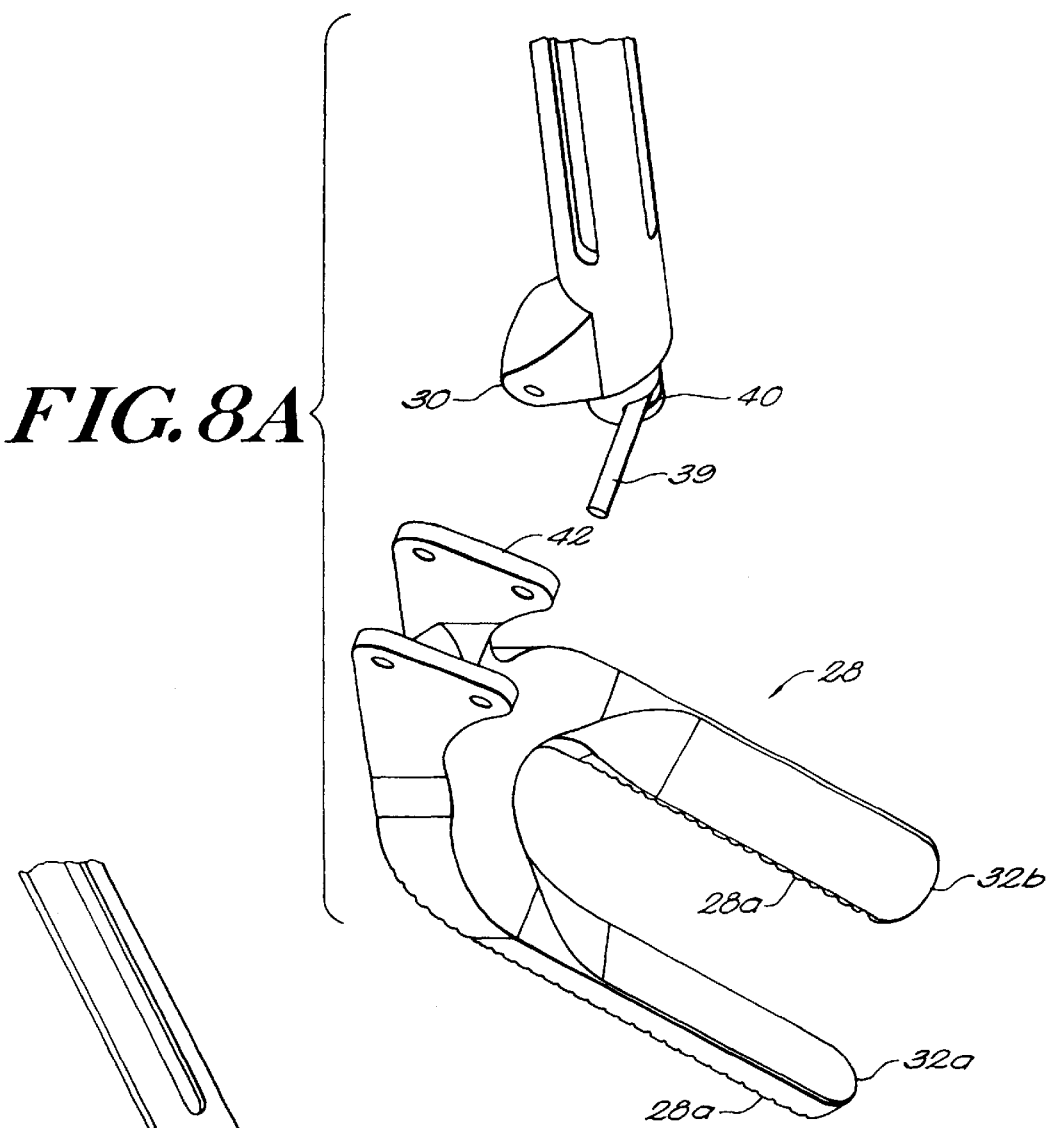
FIG. 8A is an exploded view of a tool shaft pivotly linked to an end-effector.
Figure 8B:
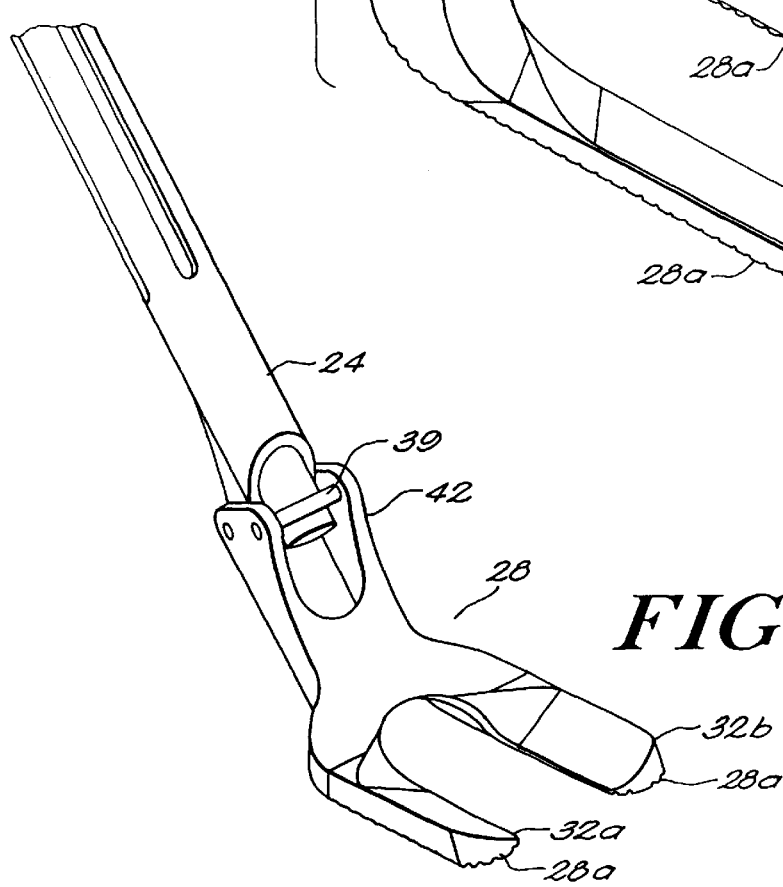
FIG. 8B is a perspective view from above of a tool shaft pivotly linked to an end-effector.

With reference to FIGS. 6 and 7, the tool holder 20 includes a selectively locking first multi-axis adjustable mounting element 22. The mounting element is adapted to grip a tool shaft. In this embodiment the mounting element is a ball and socket joint including a base 31, a screw down top 27, and a compressible mounting member 29. The mounting member is a ball with a mounting means adapted for attachment to the proximal end of a tool shaft. The screw down top has a conforming spherical shell portion 35 as an internal surface. The compressible ball has grooves 33 that divide the ball body into a plurality of deformable gripping contacts which allow for compression of the ball around the tool shaft 26. The base of the tool holder has a longitudinal slot 37 that allows selective removal and installation of the tool 26, the slot being at least the width of the tool. Thus, a tool slideably attached to the ball can be placed with an essentially horizontal motion into the base of the tool holder through the slot. Subsequently, the screw down top is placed over the tool shaft and slid down onto the base of the tool holder. By screwing the screw down top down onto the base of the tool holder the conforming spherical shell applies pressure to the ball closing or compressing the grooves and, consequently, locking the ball and tool shaft in rotational and linear position, respectively.

EXAMPLE 1

As stated above, in this embodiment of a tool according to the invention, the tool 26, depicted in FIGS. 2A–2C, 6, and 8A–10B comprises a tool shaft 24, and a end-effector 28 attached to the distal end of the tool shaft. The tool shaft includes an outer shaft 24b and an inner shaft 24c. Both shafts are hollow. The outer diameter of the inner shaft is substantially similar to the inner diameter of the outer shaft, so that they fit closely, while the inner shaft and the outer shaft are capable of motion relative to each other. The outer shaft has longitudinal slits 24a which allow the outer shaft wall to be compressed against the inner shaft.

The outer shaft has a pivot extension 30 on a distal end. The inner shaft has a pivot pin 39 and an inner shaft pivot aperture 40. The end-effector has a pivot link 42. The end-effector is pivotly attached to both the inner and outer shafts at the pivot pin and pivot extension, respectively. The pivot aperture of the inner shaft allows the pivot pin to both rotate and move transverse to the longitudinal axis of the tool shaft and transverse to the axis of the pivot pin. Movement of one shaft relative to the other thus causes articulation of the end-effector about an axis substantially parallel to the axis of the pivot pin. Furthermore, when the mounting element described above, e.g. the compressible ball 29, grips the tool shaft, the wall of the outer shaft is squeezed against the inner shaft, fixing the articulation angle of the end-effector. Thus, in one act of locking the mounting element, the tool is universally positioned and the articulation of the end-effector is fixed. In a similar manner, the tool can be configured so that relative motion of two tool shaft elements can provide rotation of an end-effector about an axis that is parallel to the tool shaft.

With reference to FIG. 9A, the illustrated end-effector 28 includes suction channels 34 channel milled into its bottom or contact side to clear the surgical field of blood and other material. Suction channel openings 36 are located on the sides of the end-effector. With reference to FIG. 6, a suction and blower tubeset 24d passes down the inside of the inner tool shaft and the blower passes out the distal end of the tool shaft. With reference to FIG. 2A, the suction tube attaches to the end-effector 28 to provide suction to the suction channels 34 milled into the end-effector 28. Thus, in one embodiment, the end-effector is a U-shaped device with two prongs 32a and 32b. Each prong includes a suction channel 34 used to clear the surgical site of blood and other material.

With reference to FIGS. 6 and 9A, the cross section profile of the end-effector is an open profile. In other words, the profile of the end-effector provides the surgeon with enhanced access to the tissue located between the prongs. In one embodiment the distance between the prongs 32a and 32b is at least about 8 to 15 mm. In another embodiment, the open profile includes a tapered cross section profile when viewed in a plane perpendicular to the prongs 32a and 32b, such that the vertical height of the prongs decreases with proximity to the surgical site.

With reference to FIGS. 8A, 8B, 9A, and 18A, in another embodiment, the contact surfaces 28a of the end-effector 28, that is the surfaces of the end-effector 28 that make contact with the surgical site, are textured. The contact surfaces are textured so as to prevent slipping and minimize movement of tissue at the surgical site relative to the end-effector.

With reference to FIGS. 9B and 9C, according to one embodiment of the invention, wire 39 with burrs 41 on its surface is imbedded in the underside 28a of an end-effector 28, 28, such that a predetermined segment of the wire is exposed on the contact surface of the end-effector. The burrs dig into tissue such that placement of the end-effector in contact with tissue allows the end effector to provide lateral or pull up tension on the tissue. Further, it allows the end effector to maintain contact with the tissue. The wire can be silver soldered into place.

Figure 10A:
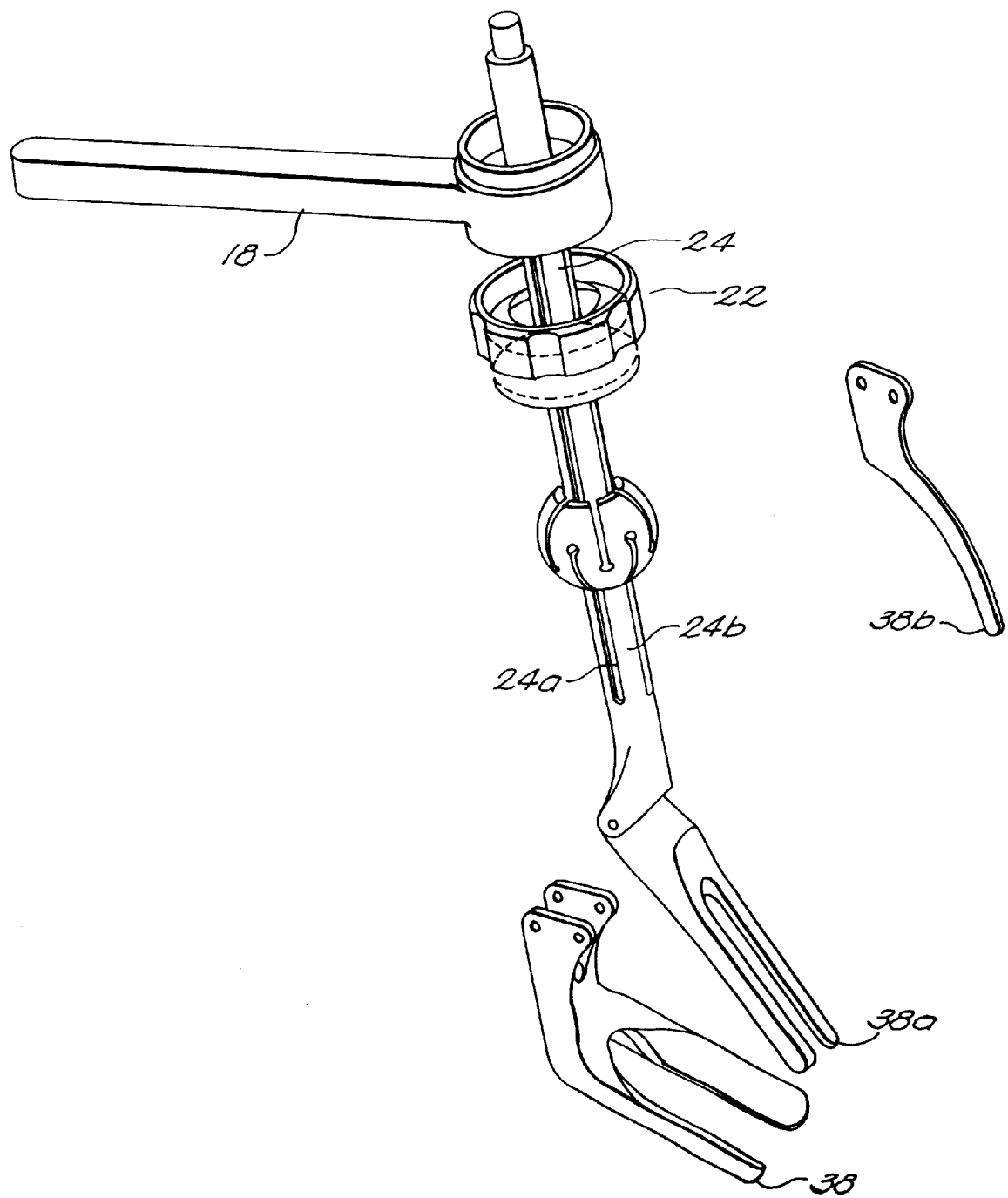
FIG. 10A is an exploded view of a tool holder with an attached tool, the tool comprising a tool shaft and an end-effector; a series of end-effectors for use with the tool shaft are also depicted.
Figure 10B:
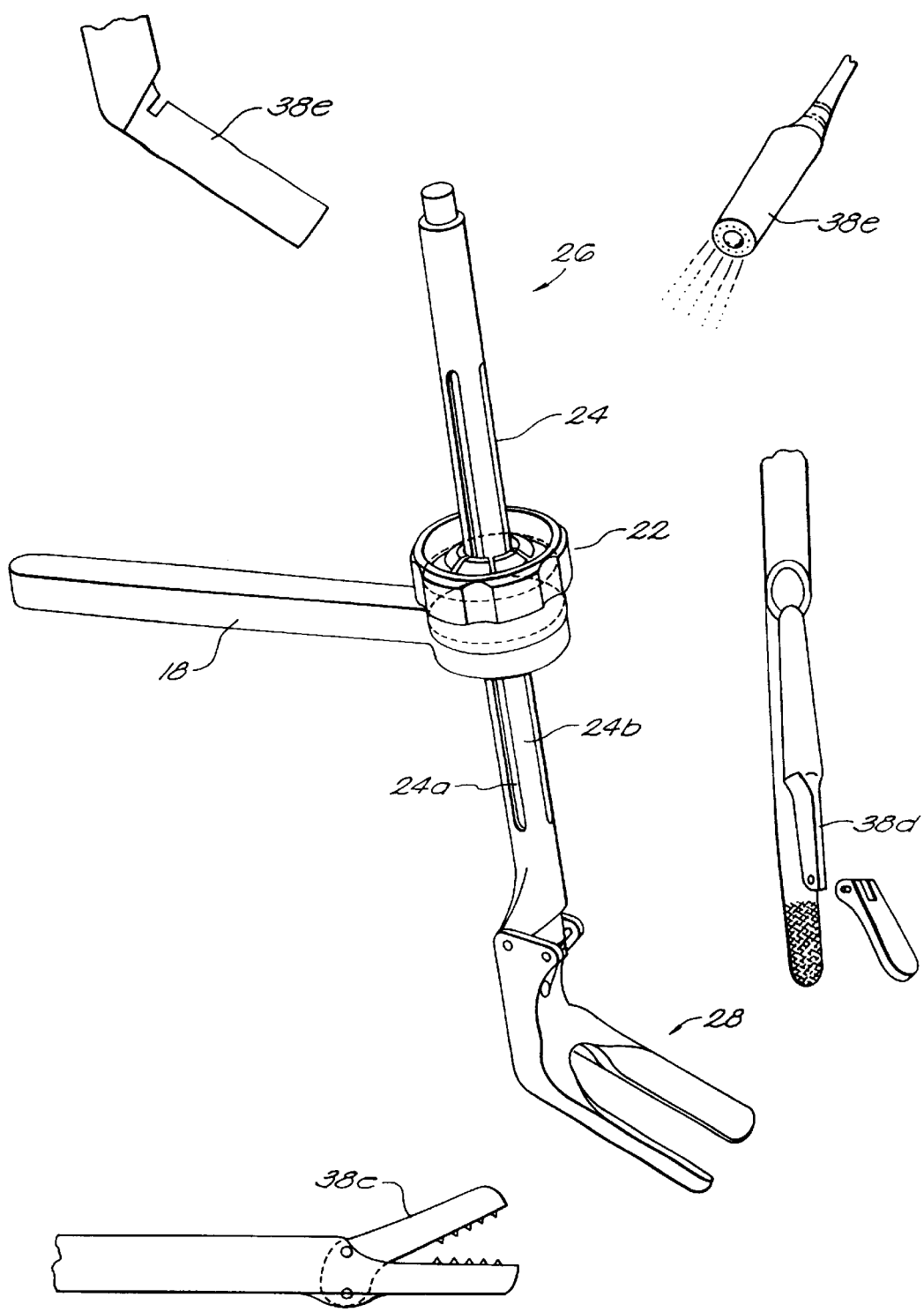
FIG. 10B shows a series of tools for use with the tool holder of FIG. 10A.
Figure 11A:
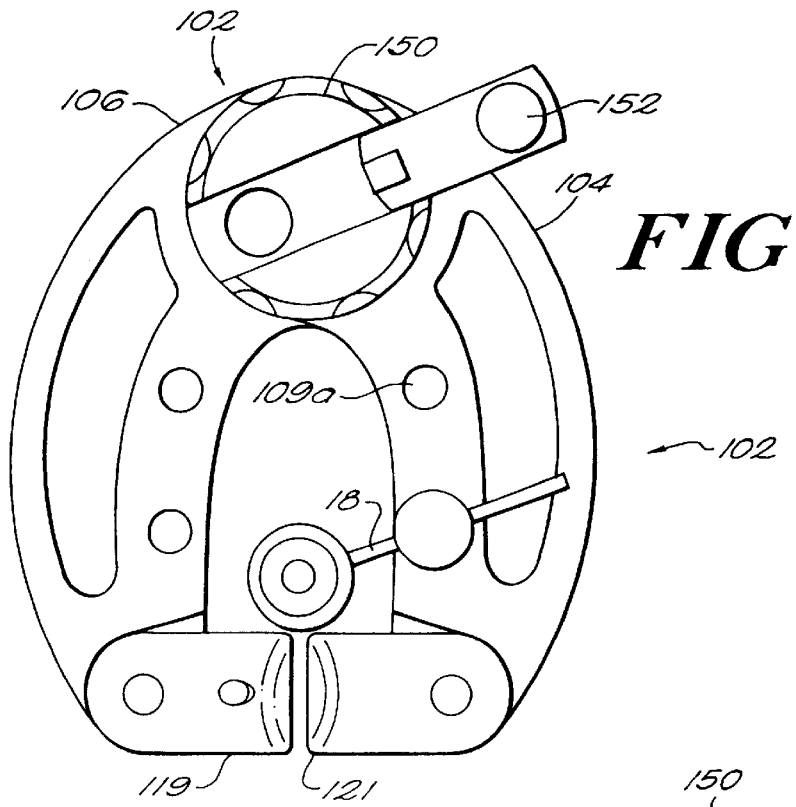
FIGS. 11A, 11B and 11C are a top plan view of a closed retractor, a perspective view from above of an open retractor, and a top plan view of an open retractor, respectively.
Figure 11B:
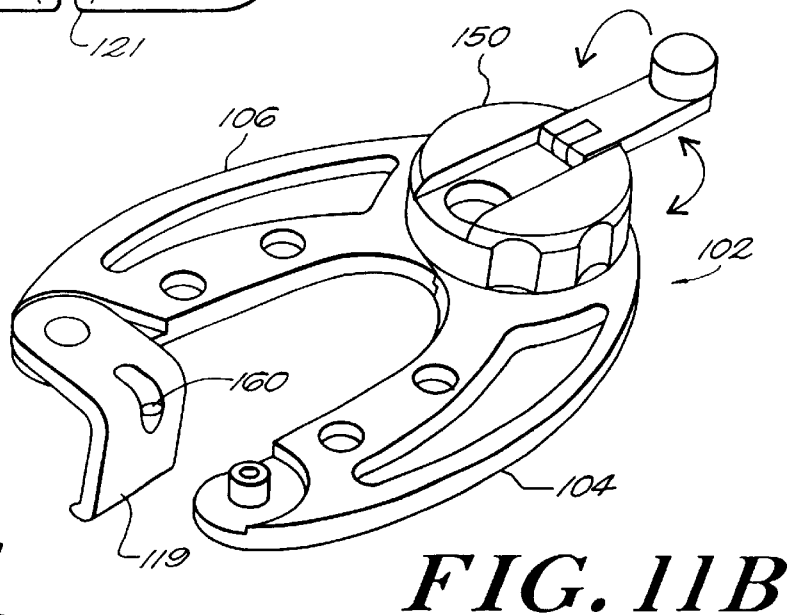
Figure 11C:
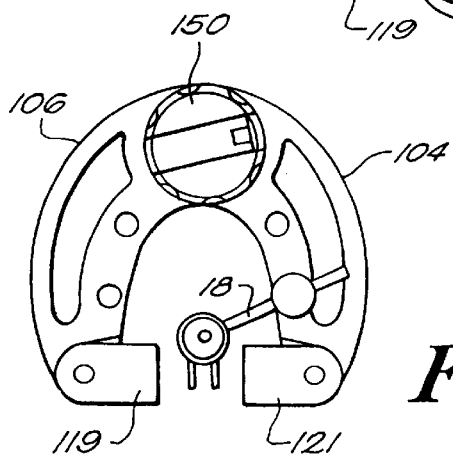

With reference to FIGS. 10A and 10B, other embodiments include different end-effectors 38, 38a, 38b, 38c, 38d, 38e, and 38f. One example of a different end-effector is a quick connect vessel occluder for stabilizing or occluding a vessel. Such a device can be used in the present invention for pinching a vessel without piercing the tissue of the heart. Other end-effectors include a hemostat, a fork, a rake to act as a retractor, a needle driver, forceps, scissors, and clip appliers. With reference to FIG. 10B, an end-effector can include an articulating camera 38e.

In another embodiment, the end-effector includes at least one clamp for the attachment of the ends of a vessel occlusion band. In order to occlude a vessel, surgeons often use a type of rubber band. A surgeon passes the band around the vessel, perhaps more than once, and then tightens the band, pinching the vessel without piercing the vessel or neighboring tissue. Commonly, a surgeon will then pull the ends of the band out of the incision and tie them down. In this embodiment, the end-effector includes a clamp so that a surgeon may tie the ends of a vessel occlusion band to the end-effector maintaining greater access to the surgical field.

EXAMPLE 2

Referring to FIGS. 11A–13, another embodiment of a retractor and surgical tool attachment system according to the invention comprises a retractor 102 for spreading and keeping back the walls of an incision in the patient. The retractor includes first and second retractor frame members 104 and 106. The second frame member 106 similar in configuration to the first frame member, has a toothed proximal end 157. The toothed proximal end of frame member 106 sits on the proximal end 159 of the first retractor frame member. An opening mechanism 150, sits on the proximal ends of the frame members and comprises a cover plate 155 and a series of gears 151. The gears fit into slot 143 in the second retractor frame member and a further slot 141 in the first retractor frame member. The retractor frame members pivot around a shaft 161 extending down from the cover plate. The cylindrical shaft inserts in slots 163 and 165 of second retractor frame and first retractor frame, respectively. The opening mechanism and gears comprise an overhead gear assembly with a ratchet system to maintain the retractor in a set position. The cover plate comprises a crank handle 152, a ratchet switch 154, and a ratchet lock pin 156. Depending on the setting of the ratchet switch the retractor can be alternatively opened and closed by turning the crank handle, rotating the gear assembly, and rotating the second retractor frame member.

Attached to the retractor frame members are modular retractor blades 119 and 121. With reference to FIG. 16C, the modular retractor blade 121 is connected to retractor frame member 104 by placement of the retractor blade 121 in the retractor frame member slot 379. Insertion of the retractor screw 380 into a retractor blade cylindrical slot 391 secures the retractor blade 121 to the retractor frame member 104. As indicated in FIG. 16C, retractor blade 119 secures to retractor frame member 106 in a similar fashion.

The retractor blades can be deflectable. With reference to FIG. 12C, the retractor blade can pivot about a pivot point 168, so that the blades can fit flush to the walls of an incision.

The blades can be soft so as to apply pressure evenly on the walls of an incision. By applying even pressure on the walls of the incision, soft retractor blades reduce surgical trauma. According to one embodiment of the invention, the retractor blade can comprise a disposable elastomeric cushion attachment 162, shown in FIG. 12C.

With reference to FIGS. 11A–13, the retractor may also incorporate a fiber optic light assembly 195, the fiber optic light assembly comprises a light source 193 and at least one optic fiber 164. The optic fiber runs along the side of the retractor frame member opposite the incision to the distal end of the retractor frame member, down below the retractor blade, and out the fiber optic exit 167. The output end 165 of the optic fiber located proximate to fiber optic exit 167 emits light so as to illuminate the inside of the body cavity.

Figure 12A:
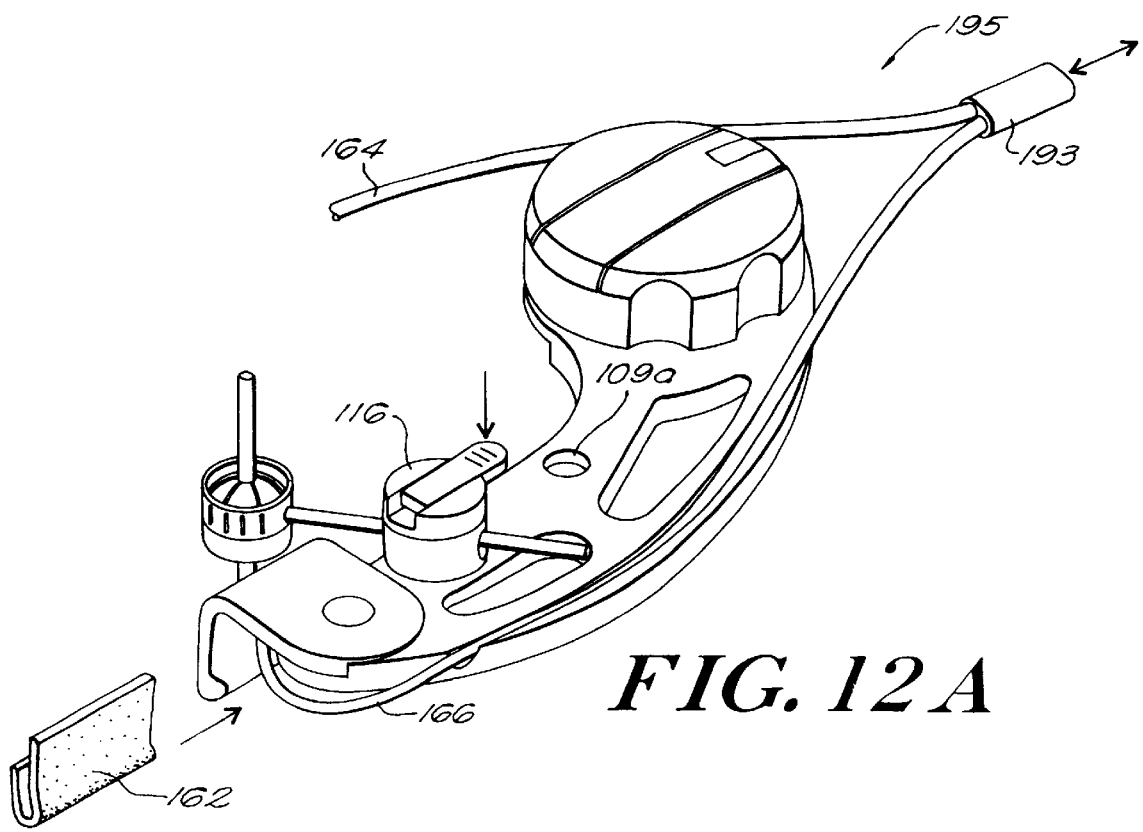
FIGS. 12A, 12B, and 12C are a perspective view from above of an extension device attached to a retractor, a cross-section view of a clamp assembly, and a cross-section view of a retractor frame member and retractor blade, respectively.
Figure 12B:
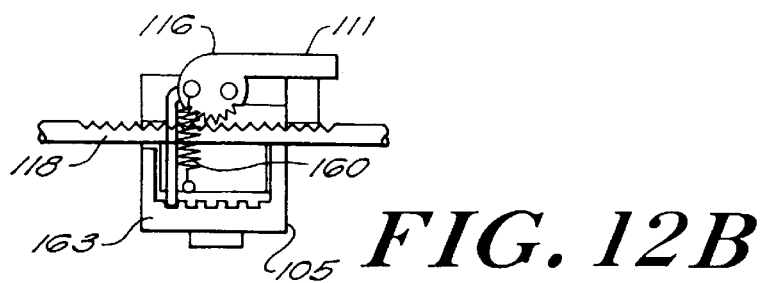
Figure 12C:
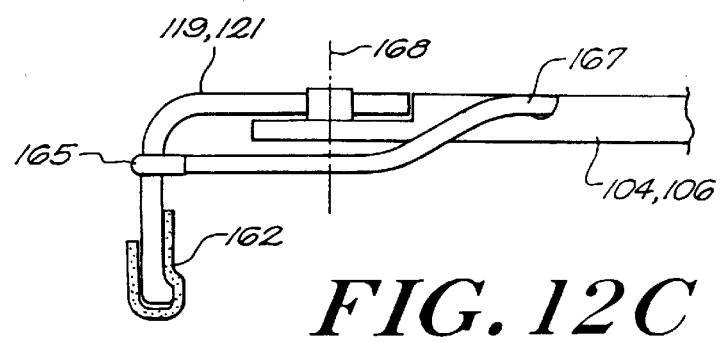
Figure 13:
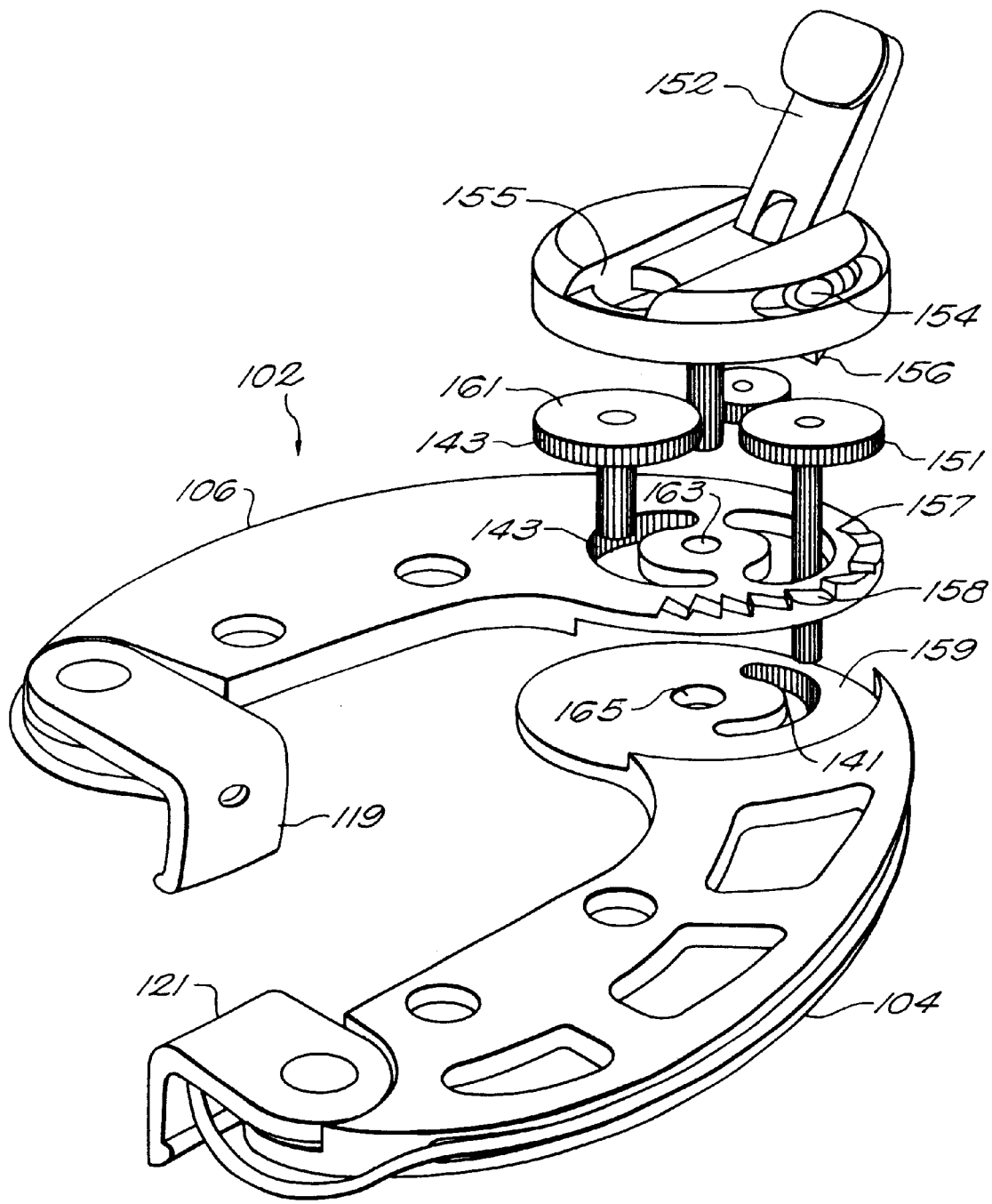
FIG. 13 is an exploded view of a retractor opening mechanism.
Figure 14A:
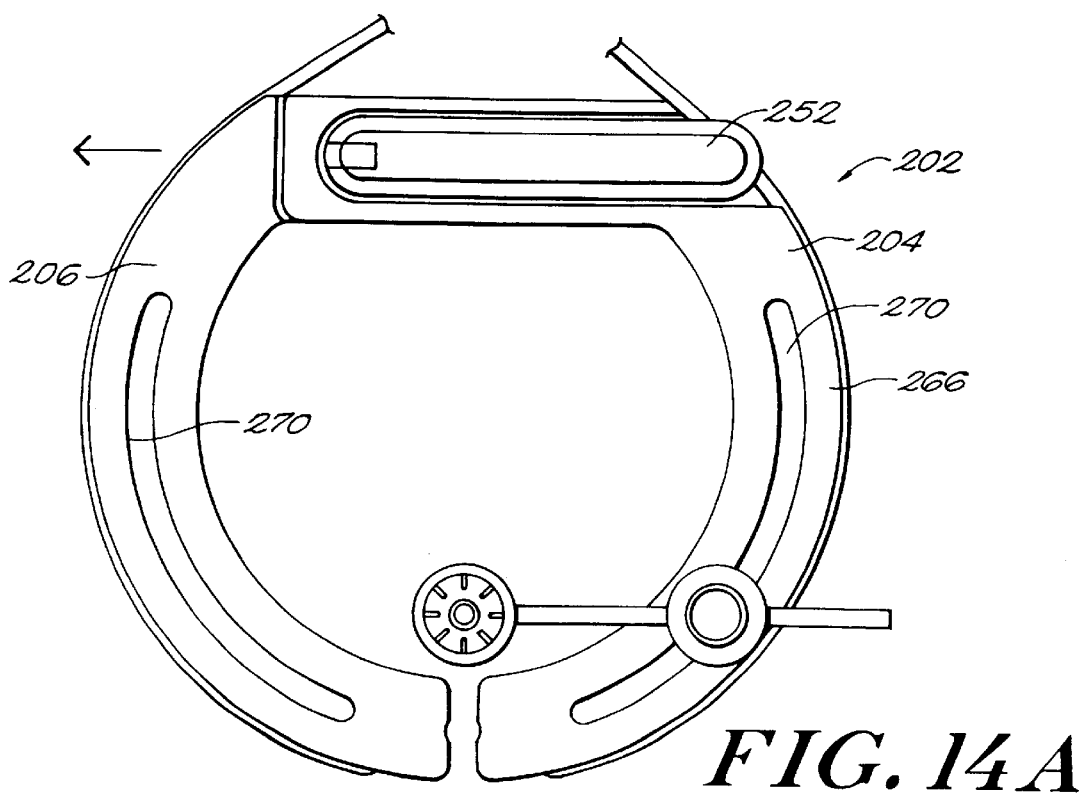
FIGS. 14A, 14B, and 14C are a top plan view of the retractor, a cross-sectional view of the retractor with a push-button clamp assembly attached, and perspective view from above of an L-shaped stationary section of the retractor with a toothed cross bar, respectively.
Figure 14B:
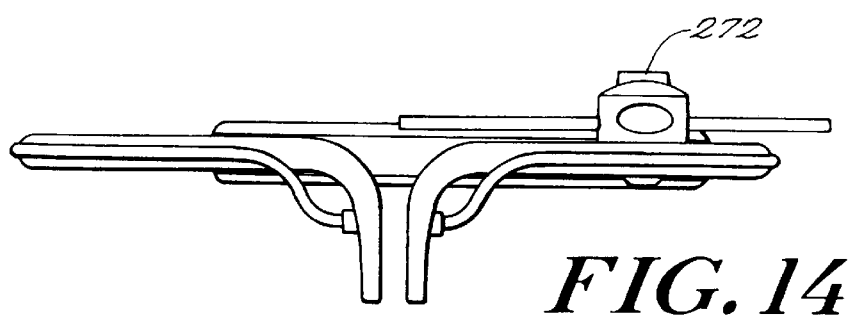
Figure 14C:
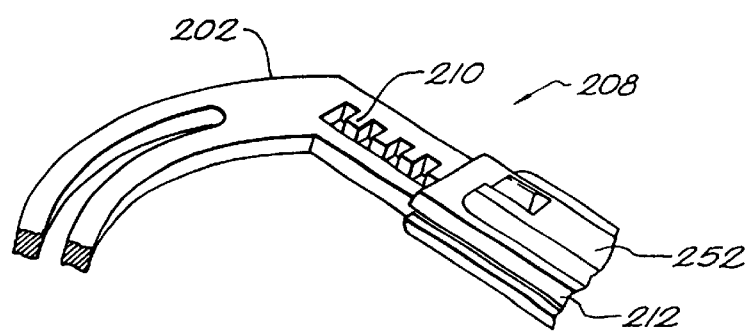
Figure 15B:
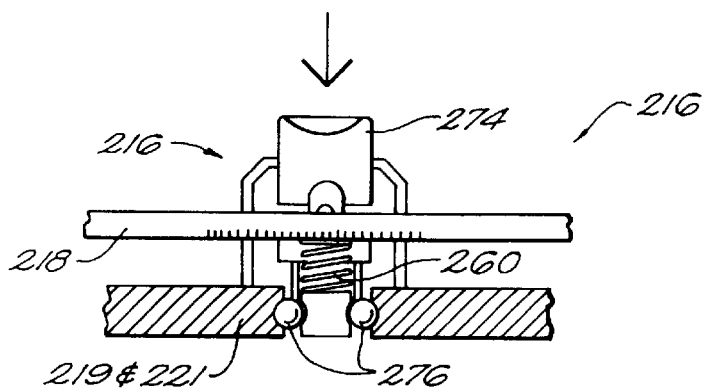
FIGS. 15A and 15B are a perspective view from above of a retractor with an extension device attached, and a cross-section view of a push-button clamp assembly, respectively.
Figure 15A:
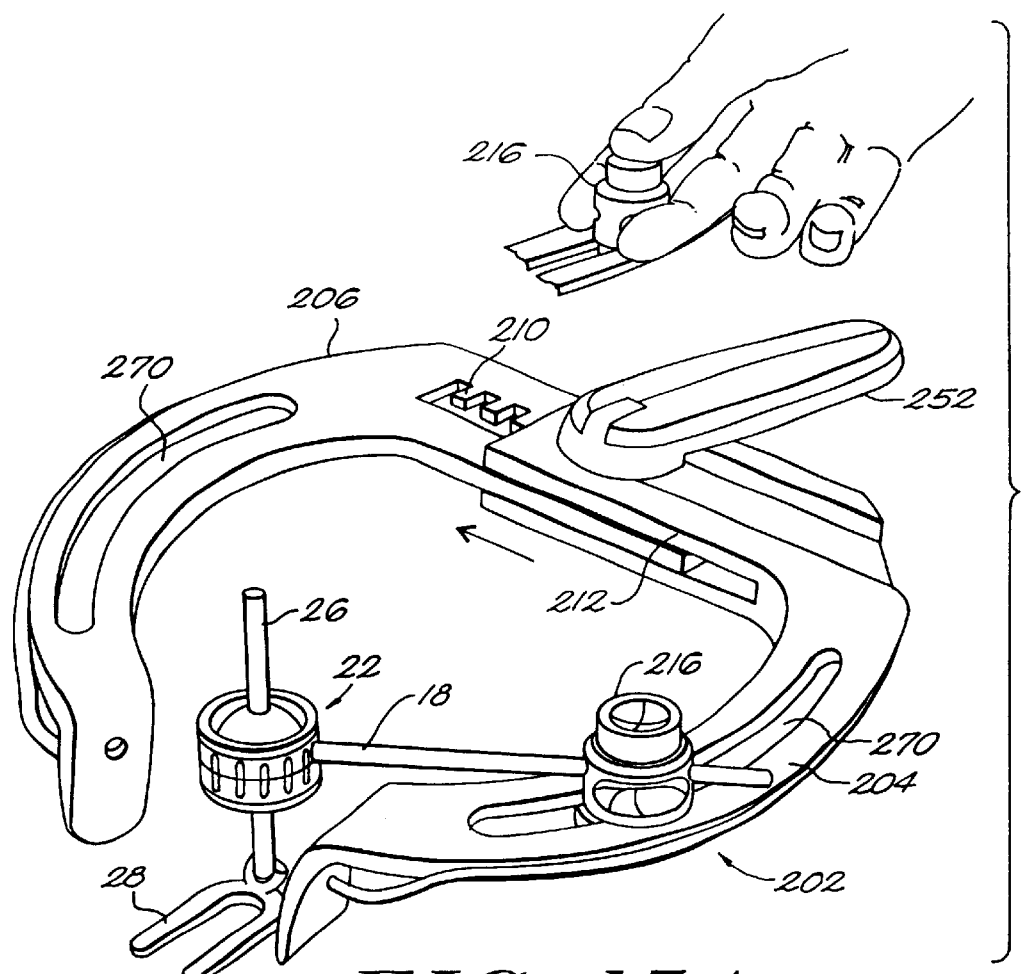

With reference to FIGS. 12A and 12B, the clamp assembly is a cam lever clamp assembly 116. A cam lever clamp assembly is spring loaded such that pushing down on the locking lever 111 locks the clamp assembly in rotational position and the positioning arm in linear position. By subsequently pushing on the locking lever 111, the clamp assembly is released allowing freedom of rotation of the clamp assembly and linear motion of the positioning arm.

The spring loaded clamp assembly achieves its functionality in the following way. The clamp assembly comprises spring 160, pin 161, and grooves 163. When the locking lever is in the up and open position, the pin is pulled out of the grooves so as to allow rotation of the clamp assembly. Furthermore, when the locking lever 111 is in the up and open position, the cam end 103 does not apply pressure to the positioning arm 118 allowing linear motion of the positioning arm. However, when the locking lever is in the down and closed position the pin is inserted in the grooves preventing rotation or motion of the clamp assembly. Further, the cam end 103 places pressure on the positioning arm preventing linear motion of positioning arm.

With reference to FIG. 12A, according to one embodiment of this invention, conforming cylindrical slots 109a are provided on the retractor frame members to allow alternative positioning of the extension device. By placing the extension device in the appropriate conforming cylindrical slot, a surgeon is able to position the extension device, and consequently the surgical tool, in an appropriate location while minimizing obstruction caused by the extension device and tool.

EXAMPLE 3

With reference to FIGS. 14A–15B, an embodiment of the retractor and surgical tool attachment system according to the invention comprises a retractor 202. The retractor includes a substantially L-shaped stationary section 208 which has a stationary frame member 204 and a moveable frame member 206. The moveable frame member, similar in configuration to the stationary frame member, has a toothed cross bar or rack 210 attached to it. The stationary frame member has a housing 212, which slides on the rack. The substantially L-shaped stationary section also includes an opening mechanism crank lever 252. Rotating the crank lever rotates a gear in the toothed cross bar of the moveable frame member alternatively moving the moveable frame member in or out.

Both frame members include universal mounting grooves 270. These mounting grooves allow an extension device 213 to be slideably positioned along the frame member within the groove.

The extension device includes a push-button clamp assembly 216. The push-button clamp assembly includes a push-button 274, a spring 160 and ball bearings 276. The push-button clamp assembly functions in the following way. When the push-button is pushed the positioning arm is released and the ball bearings loosen. When the ball bearings loosen the clamp assembly is free to rotate. However, upon pushing the push-button again the positioning arm is captured and the clamp assembly is locked in rotational position.

EXAMPLE 4

Referring to FIGS. 16A–17B, another embodiment of a retractor and surgical tool attachment system according to the invention comprises a retractor 302. The retractor incorporates the general shape of Example 2 with the universal mounting groove of Example 3. The opening mechanism comprises a foldaway crank lever 352 a gear 357 attached to the crank lever, and, a cover plate 355. The retractor comprises a first retractor frame member 304 and a second retractor frame member 306. The proximal end of the second retractor frame member sits on top of the proximal end of the second retractor frame member. The opening mechanism sits on the proximal ends of the frame members 304 and 306. The proximal end of the second retractor frame member 306 has a slot 393 with ratchet teeth 392. The gear 357 of the opening mechanism fits in the slot 393 of the second frame member 306. By turning the crank lever 352 which is attached to the opening mechanism gear 357, the gear 357 rotates against the ratchet teeth 392 of the slot 393 of the proximal end of the second frame member 306, causing the second frame member 306 to rotate about the axis 397. The rotation of the second retractor frame member 306 causes the retractor 302 to open and spread apart an incision.

This embodiment incorporates a fiber optic routing assembly 379. The fiber optic routing assembly comprises an opening mechanism sheath 379a, optical fiber 364, and fiber optic light balls 377. One end of the optical fiber is connected to a light source. Light travels down the optical fiber, from the light source, into the opening mechanism sheath, and to the light balls, illuminating the surgical field. Further, another optical fiber 366, is mounted in a fiber optic track 398 located on the outside of retractor frame member 304. The optical fiber extends down below retractor member 304 and out to retractor blade 321, through the fiber optic exit 360. Again, light from a light source travels along the optical fiber 366 and is emitted at the fiber optic exit 360, further illuminating the surgical field.

Figure 16A:
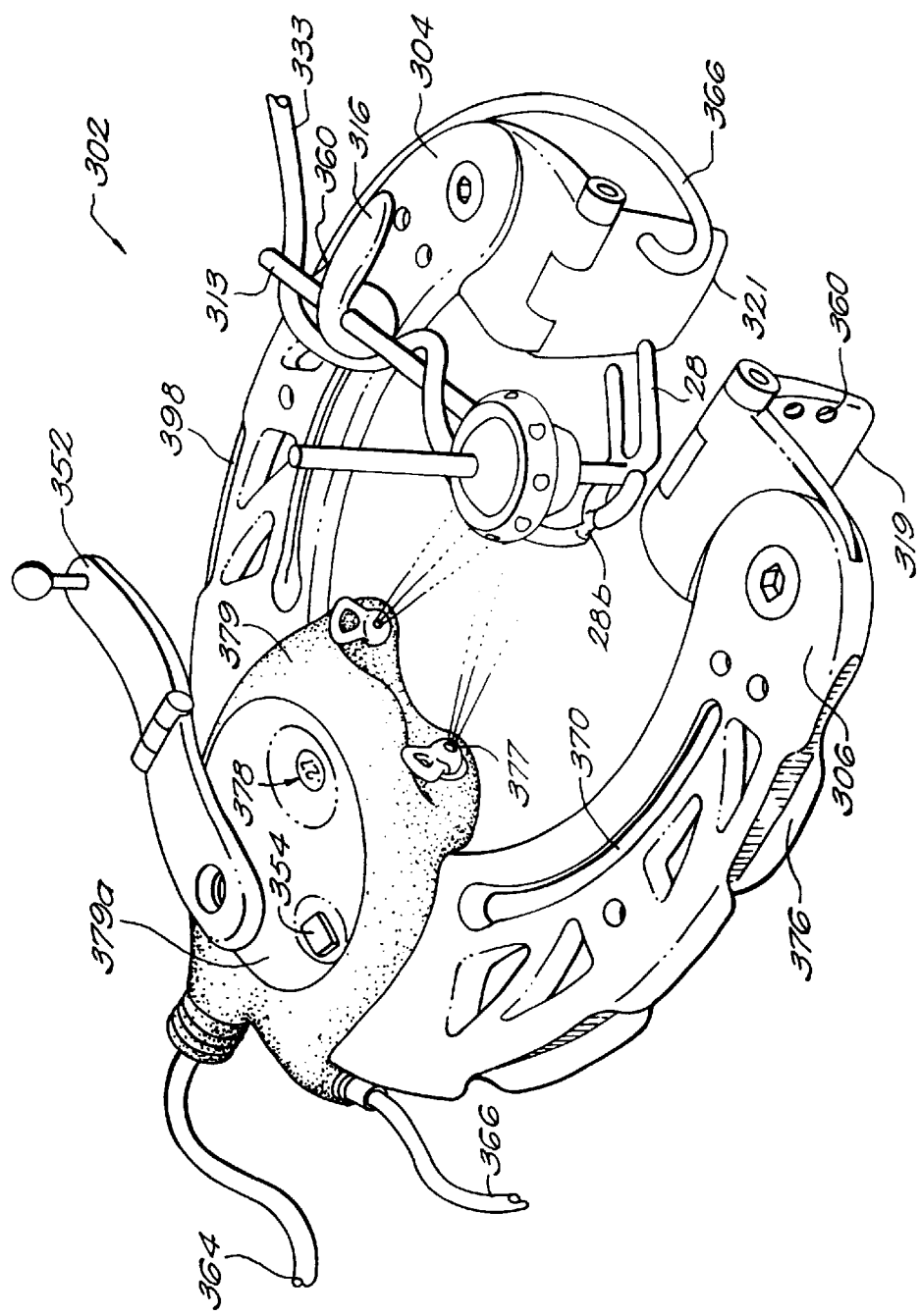
FIGS. 16A, 16B, and 16C are a perspective view from above of a retractor with an extension device attached, an exploded view of a retractor opening mechanism, and an exploded view of a retractor blade attachment to a retractor frame member, respectively.
Figure 16C:
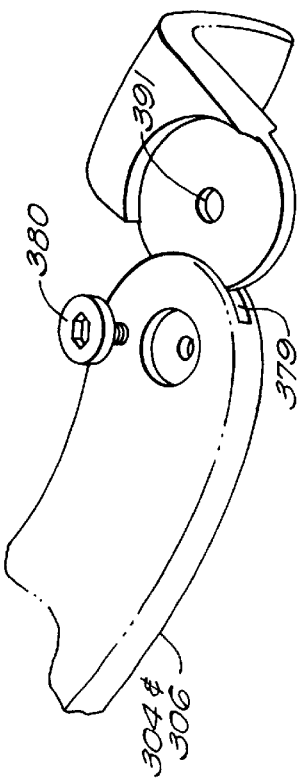
Figure 16B:
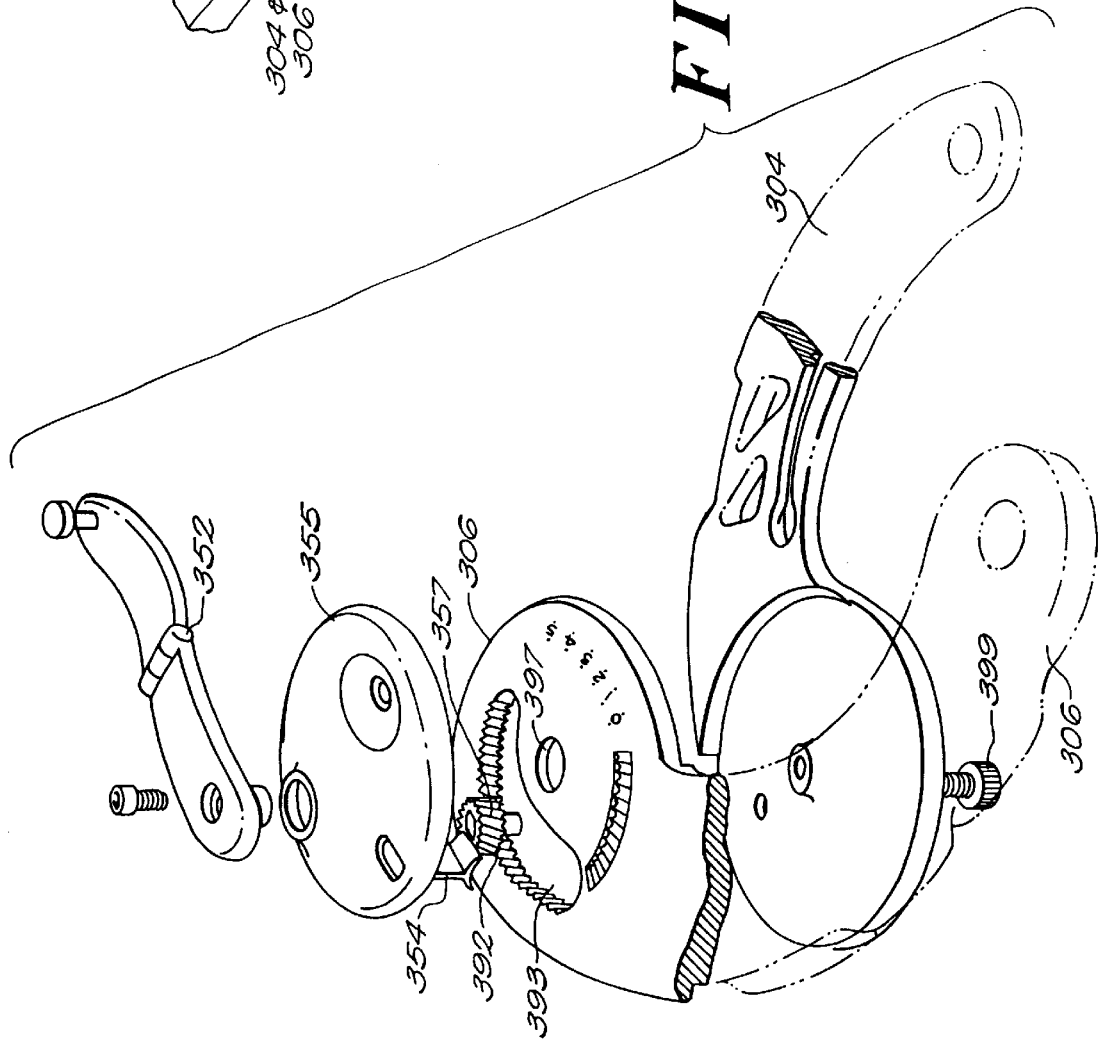
Figure 17A:
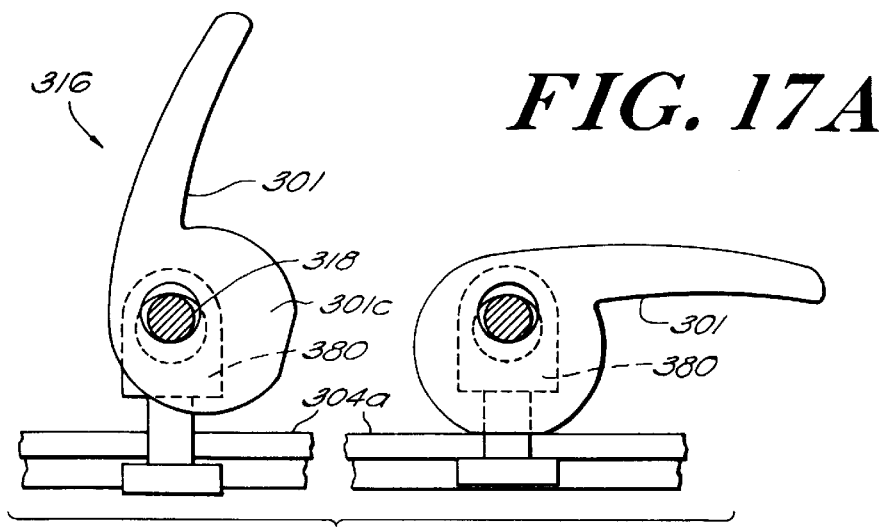
FIGS. 17A, 17B, and 17C are a cross-sectional view of a cam lock in the open and locked positions, an exploded view of a cam lock, guide pin and retractor frame member, and a perspective view from above of a cam lock clamp assembly, respectively.
Figure 17B:
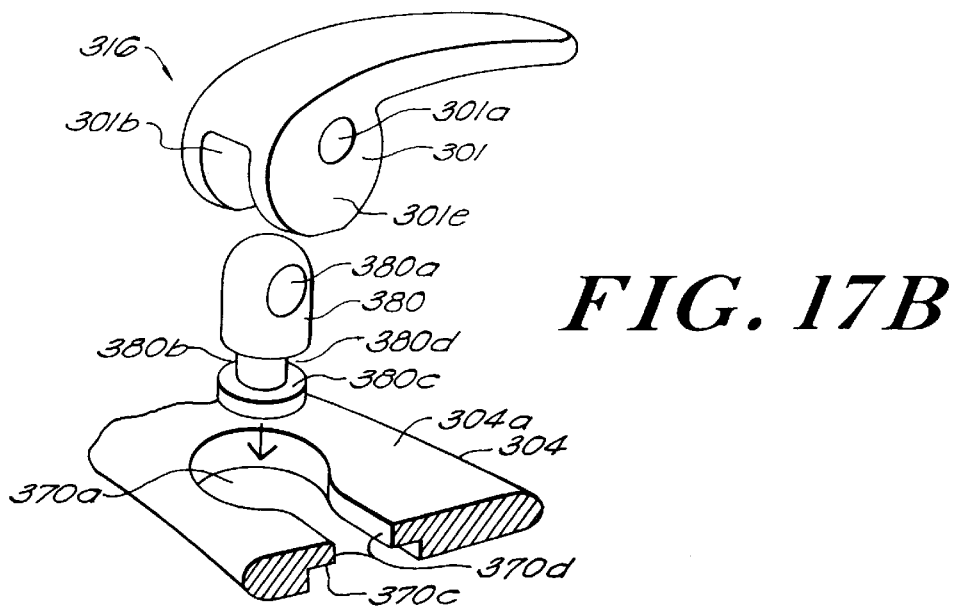
Figure 17C:
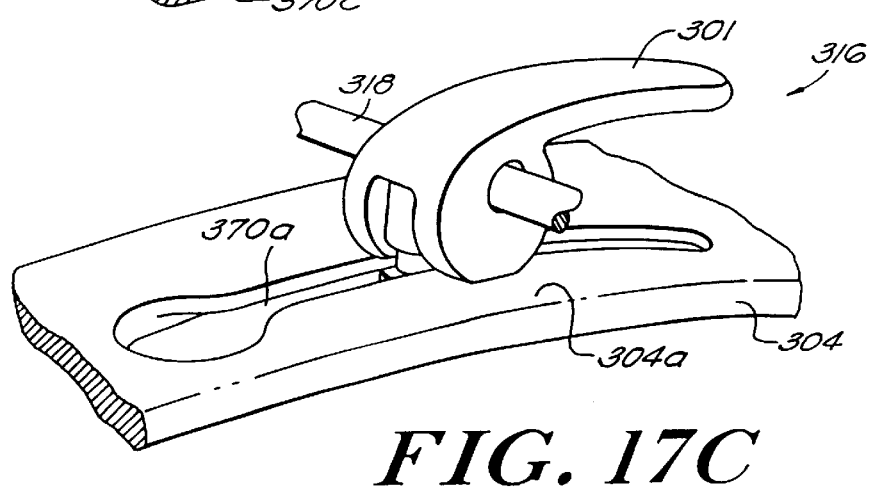

With reference to FIGS. 2A and 16A, this embodiment also incorporates the ability to apply suction to the surgical field to remove blood and other material. The suction assembly comprises suction tubing 333 attached at one end to a suction pump and at the other end to an end-effector 28 via tubing attachments 28b. The suction tubing could pass down the center of a tool shaft or down along side a tool shaft.

Another embodiment incorporates the ability to blow on the surgical field. A blower comprises blower tubing similar to the suction tubing 333. The tubing is a fully soft, unannealed material with a wire backbone to allow positioning.

Referring to FIGS. 16A, and 17A–17C, the extension device includes a cam lock clamp assembly 316. The cam lock clamp assembly includes a cam lock 301 and a guide pin 380. The head of the guide pin 380 fits into the cam lock guide pin slot 301b. The positioning arm 318 slides through the cam lock 301 and guide pin 380 positioning arm slots, 301a and 380a, respectively. The guide pin 380 is inserted in the universal mounting groove aperture 370a, such that the edges 370d of the universal mounting groove 370a slide in the universal mounting groove slot 380d of the guide pin 380. Thus, the guide pin 380 of the cam lock clamp assembly 316 can be located anywhere in the universal mounting groove 370a. The cam lock 301 can be rotated and the positioning arm 318 can move linearly when the locking lever 301 is in the up and open position.

Upon lowering the locking lever 301 to the down position the cam lock clamp assembly 316 is locked. The locking lever 301 rotates the cam lock about an axis that is substantially parallel to axis 318a. The end 301c of the cam locking lever 301 is aspherical such that pushing the locking 301 to the closed position forces the bulbous end 301c of the cam locking lever 301 down against the retractor frame member 304a. Because of the interaction of the positioning arm, cam lock, and guide pin, the guide pin bottom 380c is forced up against the universal mounting groove surface 307c. The pressure between the guide pin bottom 380c and the universal mounting groove surface 370c prevents the cam lock clamp assembly 316 from rotating. Furthermore, the pressure between the cam lock 301 and the positioning arm 318, and the guide pin 380 and the positioning arm 318 prevents the positioning arm 318 from moving linearly.

EXAMPLE 5

Referring to FIGS. 9A, and 18A–18C, another embodiment of an end-effector tool shaft attachment is illustrated comprising a swivel link 482. The swivel link comprises cylindrical swivel link 482 rods 482a which attach to conforming slots 427a and 427b in first and second tool shaft 426 section 426a and 426b, respectively. The swivel link 482 has an end-effector attachment 484 that connects to a conforming end-effector slot 482b. Thus, relative motion of the first and second tool shaft sections 426a and 426b causes a rotation of the swivel link 482 about an axis 499. This rotation of the swivel link 482 causes rotation of the end-effector 28.

The above embodiments according to the invention have several advantages. Heart stabilization assemblies which attach to a retractor are superior to hand held devices because an assistant's hands are not in the way and because they are more effective in limiting the motion of the heart. A surgeon can rapidly place a surgical tool using this invention. Furthermore, this embodiment allows the surgeon to rapidly remove the tool, restoring access to the surgical arena.

This invention allows easier and more complete access to the surgical field defined by the retractor because the position of the surgical tool is completely independent of the retractor. This position independence is useful. As described above, when a heart surgeon opens a surgical cavity and places a retractor, the patient's heart is covered with an opaque tissue. Unable to clearly determine the location of the artery, the surgeon must approximate the location of the artery and place the retractor accordingly. Upon removing the opaque tissue and discovering that the artery is not located near the center of the retractor, it be necessary to adjust the position of the end-effector. Because the position of the tool is completely independent of the retractor, the surgeon merely adjusts the tool over the artery of interest. The ability to adjust the location of the tool without adjusting the position of the retractor will reduce the time, cost, and trauma of surgery.

Further, the surgeon is free to determine the insertion point and the insertion angle of the tool. This freedom is important because it allows the surgeon to place the tool near the edge of the incision and at an appropriate angle so as to provide the surgeon with greater access to the surgical field. Thus, this invention provides a surgeon with flexibility. This invention can be used in many operations including LAD coronary artery operations and valve replacement operations.

Importantly, this invention improves minimally invasive direct surgery. The invention allows a surgeon to place a tool effectively anywhere in the surgical field, articulate the end-effector, and freeze the position of the tool and the articulation of the end-effector in one act, the locking of the mounting element.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed is:

1. A surgical retractor, comprising
   an adjustable frame for engaging patient tissue and for spreading open an incision in said tissue in substantially a first plane, to create a surgical field,
   an extension device mounted to said adjustable frame and being selectively moveable with respect to said adjustable frame and having first and second ends,
   wherein said extension device further comprises a positioning arm adjustably coupled to said frame and having first and second ends, wherein said first end is adapted for mounting to said adjustable frame, and said second end is adapted for mounting to a tool holder,
   wherein said adjustable frame includes two frame members each having first and second ends, said first ends of said frame members being mechanically coupled for varying, a spatial proximity between said second ends of said frame members,
   wherein said first ends of said frame members are mechanically coupled for pivoting about an axis substantially transverse to said first plane,
   a worm gear assembly, coupled to said first ends of said frame members, to adjust said spatial proximity between said second ends of said frame members.

2. A surgical retractor, comprising
   an adjustable frame for engaging patient tissue and for spreading open an incision in said tissue in substantially a first plane, to create a surgical field,
   an extension device mounted to said adjustable frame and being selectively moveable with respect to said adjustable frame and having first and second ends,
   wherein said extension device further comprises a positioning arm adjustably coupled to said frame and having first and second ends, wherein said first end is adapted for mounting to said adjustable frame, and said second end is adapted for mounting to a tool holder,
   wherein said adjustable frame includes two frame members each having first and second ends, said first ends of said frame members being mechanically coupled for varying, a spatial proximity between said second ends of said frame members.
   wherein said first ends of said frame members are mechanically coupled for pivoting about an axis substantially transverse to said first plane,
   an overhead gear assembly with a ratchet system, coupled to said frame members, to adjust said spatial proximity between said second ends of said frame members.

3. A surgical retractor according to claim 2, further comprising a foldaway crank lever coupled to said overhead gear assembly.

4. A surgical retractor, comprising
   an adjustable frame for engaging patient tissue and for spreading open an incision in said tissue in substantially a first plane, to create a surgical field, said adjustable frame comprising;
   two frame members each having first and second ends, said first ends of said frame members being linear and aligned with each other, thereby adapted to slide along each other for varying a spatial proximity between said second ends of said frame members,
   an extension device mounted to one of said frame members,
   a push-button clamp assembly mounted between said extension device and said one of said frame members,
   wherein said extension device further comprises a positioning arm coupled to said frame and having first and second ends, wherein said first end is adapted for mounting to said adjustable frame, and said second end is adapted for mounting to a tool holder,
   wherein said tool holder comprises a locking multi-axis adjustable mounting element mounted to said second end of said positioning arm and adapted to pivotably locate a tool shaft relative to said extension device.

5. A surgical retractor according to claim 4, and further comprising, opening means for adjusting said spatial proximity between said second ends of said first and second frame members.

6. A surgical retractor according to claim 4, further comprising
   a gear rotatably coupled to said first end of said second frame member, and
   a crank lever mounted to said gear to rotate said gear, wherein said first frame member further comprises a toothed rack, in which said gear is located for engaging said toothed rack for effectuating said varying of said spatial proximity between said second ends of said first and second frame members upon rotation of said crank lever.

7. A surgical retractor comprising an adjustable frame for engaging patient tissue and for spreading open an incision in said tissue longitudinal to a first plane, to create a surgical field, said adjustable frame having, two frame members each having first and second ends, said first ends of said frame members being mechanically coupled for varying a spatial proximity between said second ends of said frame members by rotating within a second plane longitudinal to said first plane, and an extension device mounted to one of said frame members and extending in a direction toward the other of said frame members, wherein said extension device further comprises a positioning arm coupled to said frame and having first and second ends, wherein said first end is adapted for mounting to said adjustable frame, and said second end is adapted for mounting to a tool holder, wherein said tool holder comprises a locking multi-axis adjustable mounting element mounted to said second end of said positioning arm and adapted to pivotably locate a tool shaft relative to said extension device.

8. A surgical retractor according to claim 7 further comprising opening means for adjusting said spatial proximity between said second ends of said frame members.

9. A surgical retractor according to claim 7, wherein each of said second ends of said frame members is adapted for removable and replaceable mounting attachment of a blade member, and wherein said blade members are adapted for engaging tissue proximate to the incision to facilitate said spreading.

10. A surgical retractor according to claim 9, wherein said blade members are adapted for pivoting about an axis substantially normal to said second plane.

11. A surgical retractor according to claim 9, wherein each of said blade members is adapted for removable and replaceable mounting of a compliant blade element having a tissue engaging surface for contacting the tissue proximate to the incision, and for substantially evenly distributing a contact pressure along said tissue engaging surface.

12. A surgical retractor according to claim 7, wherein said positioning arm is removably and replaceably mounted to said adjustable frame.

13. A surgical retractor according to claim 7 further comprising a clamp assembly mounted between said adjustable frame and said positioning arm.

14. A surgical retractor according to claim 13, wherein said clamp assembly further includes locking means for locking said positioning arm in a selectable stationary position with respect to said adjustable frame.

15. A surgical retractor according to claim 14, wherein said first and second ends of said positioning arm define a first longitudinal axis, and said clamp assembly further includes axial positioning means for slideably and lockably positioning said second end of said positioning arm at a selected point along said first longitudinal axis.

16. A surgical retractor according to claim 14, wherein said adjustable frame includes a top surface contacting said locking means, a rotational axis is defined by a line normal to said top surface and intersecting said positioning arm, and wherein said clamp means further includes rotational position means for rotatably and lockably positioning said positioning arm at a selected rotational angle with respect to said rotational axis.

17. A surgical retractor according to claim 7 and further comprising a tool holder mounted to said second end of said positioning arm.

18. A surgical retractor according to claim 17, further comprising a tool shaft mounted to said tool holder, wherein a first end and a second end of said tool shaft define a second longitudinal axis, and said tool holder further includes means for enabling said tool shaft to slide along said second longitudinal axis, and a locking assembly for securing said extension device in a selected position along said second longitudinal axis.

19. A surgical retractor according to claim 18, wherein said tool shaft includes a first hollow structure adapted for coupling at least one of a suction source and a blower source from said second end to said first end.

20. A surgical retractor according to claim 19, further comprising an end-effector mounted to an end of said tool shaft located closest to said first plane, wherein said end-effector includes a tissue engaging surface and is adapted for coupling at least one of said suction source and said blower source to said tissue engaging surface.

21. A surgical retractor according to claim 18, further comprising, an end-effector mounted to a first end of said tool shaft located closest to said first plane, wherein said first end of said tool shaft is adapted for selectively rotating a mounted end-effector about said longitudinal axis.

22. A surgical retractor according to claim 21 further including means for locking a mounted end-effector in a selected rotational position with respect to said tool shaft.

23. A surgical retractor according to claim 22 further including means for locking a mounted end-effector in a selected transverse position with respect to said tool shaft.

24. A surgical retractor according to claim 21, wherein said first end of said extension device is adapted for selectively moving a mounted end-effector in a transverse direction with respect to said tool shaft.

25. A surgical retractor according to claim 18, further comprising an end-effector mounted to an end of said tool shaft located closest to said first plane wherein said end-effector includes first and second opposing prongs, wherein said prongs define a portion of a perimeter around said surgical field.

26. A surgical retractor according to claim 25, wherein said opposing prongs of said end-effector include a textured tissue engaging surface for reducing slippage between said tissue engaging surface and tissue contacted in said surgical field.

27. A surgical retractor according to claim 26, wherein said textured surface includes burrs.

28. A surgical retractor according to claim 18, further comprising an end-effector mounted to an end of said tool shaft located closest to said first plane wherein said end-effector is a vessel occluder for pinching a vessel.

29. A surgical retractor according to claim 18, further comprising an end-effector mounted to an end of said tool shaft located closest to said first plane wherein said end-effector is one of a hemostat, a fork, a rake retractor, a needle driver, forceps, scissors, and clip appliers.

30. A surgical retractor according to claim 17, wherein said tool holder further includes means for enabling said tool shaft to pivot about said tool holder.

31. A surgical retractor according to claim 7, further comprising a light coupled to said adjustable frame, oriented to illuminate an area of interest within said surgical field.

32. A surgical retractor according to claim 7 further comprising means for coupling a fiber optic light source along at least one of said first and second frame members.

33. A surgical retractor according to claim 32, wherein said means for coupling said fiber optic light source includes a light guide mounted along said at least one frame member, and adapted for removable and replaceable mounting of a disposable light wand at an end of said light guide proximate to said second end of said at least one frame member.

34. A surgical retractor according to claim 7, further comprising means for coupling a suction source to said adjustable frame, for providing a mechanism for clearing material out of said surgical field.

35. A surgical retractor according to claim 7 further comprising means for coupling a suction source along at least one of said first and second frame members.

36. A surgical retractor according to claim 35, wherein said means for coupling said suction source includes a tube mounted along said at least one frame member and extending into said surgical field.

37. A surgical retractor for spreading an incision of tissue located longitudinal to a first plane, comprising
first and second frame members coupled to each other, each frame member rotatable about at least one axis substantially normal to said first plane, and
an extension device rotatably coupled to said first frame member to travel about a further axis substantially normal to said first plane,
wherein said extension device further comprises a positioning arm coupled to said first frame member and having first and second ends, wherein said first end is adapted for mounting to said first frame member, and said second end is adapted for mounting to a tool holder,
wherein said tool holder comprises a locking multi-axis adjustable mounting element mounted to said second end of said positioning arm and adapted to pivotably locate a tool shaft relative to said extension device.

38. A surgical retractor according to claim 37, further comprising
a tool holder mounted to said extension device adapted to receive a tool shaft.

39. A surgical retractor according to claim 38, wherein said extension device further comprises
a clamp assembly rotatably mounted to said first frame member for slidably mounting said positioning arm to said clamp assembly and carrying said tool holder for disposition of the tool holder relative to the incision.

40. A surgical retractor according to claim 39, wherein said first frame member defines a mounting groove in which said clamp assembly is rotatably and slideably mounted.

41. A surgical retractor according to claim 38, further comprising
a tool shaft mounted within said tool holder adapted to extend toward said incision.

42. A surgical retractor according to claim 41, wherein said tool shaft comprises two coaxial shafts configured to move independently, and
said tool holder comprises a selectively locking multi-axis adjustable mounting element, adapted to optionally squeeze, and thereby selectively allow, or alternatively, inhibit movement of said two coaxial shafts.

43. A surgical retractor according to claim 42, further comprising
an end-effector mounted to an end of said tool shaft closest to said first plane,
wherein said end-effector is articulated by the relative movement of said two coaxial shafts.

44. A surgical retractor according to claim 43, further comprising
suction channels formed into said end-effector and adapted to be coupled to a suction source.

45. A surgical retractor according to claim 43, wherein said end-effector is formed with a tapered cross-section profile and a textured on a side opposite a side facing said first and second frame members.

46. A surgical retractor according to claim 43, wherein said end-effector is a surgical tool selected from the group consisting of a quick connect vessel occluder, a hemostat, a fork, a retractor rake, a needle driver, forceps, scissors, clip appliers, articulating camera and at least one clamp for attachment of the ends of a vessel occlusion band.

47. A surgical retractor according to claim 37, further comprising
first and second retractor blades formed at said second ends of said first and second frame members, respectively, and pivotally mounted to said frame members about an axis substantially normal to said first plane.

48. A surgical retractor according to claim 37, wherein
said first and second frame members are coupled to each other to rotatably travel about a single axis substantially normal to said first plane.

49. A surgical retractor according to claim 37, further comprising
blower tubing mounted to said frame members and oriented to blow on the incision of tissue.

50. A surgical retractor according to claims 37, further comprising
a cam lock clamp assembly rotatably coupling said extension device to said first frame member.

51. A surgical retractor according to claim 37, further comprising
a push-button clamp assembly rotatably coupling said extension device to said first frame member.

52. A surgical retractor according to claim 37, further comprising
an optical illumination assembly mounted to at least one of said frame members and oriented to illuminate the incision of tissue.

53. A surgical retractor, comprising
an adjustable frame for engaging patient tissue and for spreading open an incision in said tissue in substantially a first plane, to create a surgical field,
an extension device mounted to said adjustable frame and being selectively moveable with respect to said adjustable frame and having first and second ends,
wherein said extension device further comprises a positioning arm adjustably coupled to said frame and having first and second ends, wherein said first end is adapted for mounting to said adjustable frame, and said second end is adapted for mounting to a tool holder,
wherein said adjustable frame comprises two frame members each having first and second ends, said first ends of said frame members being mechanically coupled for varying, a spatial proximity between said second ends of said frame members, a clamp assembly to removably and replaceably lock said positioning arm to said adjustable frame, wherein said clamp assembly further includes a cam lock for alternately locking and releasing said clamp assembly.

54. A surgical retractor, comprising an adjustable frame for engaging patient tissue and for spreading open an incision in said tissue in substantially a first plane, to create a surgical field, an extension device mounted to said adjustable frame and being selectively moveable with respect to said adjustable frame and having first and second ends, wherein said extension device further comprises a positioning arm adjustably coupled to said frame and having first and second ends, wherein said first end is adapted for mounting to said adjustable frame, and said second end is adapted for mounting to a tool holder, wherein said adjustable frame includes two frame members each having first and second spaced apart ends, said first ends of said frame members being mechanically coupled for varying, a spatial proximity between said second ends of said frame members, a clamp assembly to removably and replaceably lock said positioning arm to said adjustable frame, wherein said clamp assembly further includes a mounting element, adjustable in a plurality of axes, locking said positioning arm in a selected position with respect to said adjustable frame.

55. A surgical retractor, comprising an adjustable frame for engaging patient tissue and for spreading open an incision in said tissue in substantially a first plane, to create a surgical field, an extension device mounted to said adjustable frame and being selectively moveable with respect to said adjustable frame and having first and second ends, wherein said extension device further comprises a positioning arm adjustably coupled to said frame and having first and second ends, wherein said first end is adapted for mounting to said adjustable frame, and said second end is adapted for mounting to a tool holder, wherein said adjustable frame includes two frame members each having first and second spaced apart ends, said first ends of said frame members being mechanically coupled for varying, a spatial proximity between said second ends of said frame members, a clamp assembly to removably and replaceably lock said positioning arm to said adjustable frame, wherein said clamp assembly further includes a pushbutton assembly for triggering locking of said positioning arm in said selected position, and for triggering release of said position arm from said selected position.

56. A surgical retractor, comprising an adjustable frame for engaging patient tissue and for spreading open an incision in said tissue in substantially a first plane, to create a surgical field, an extension device mounted to said adjustable frame and being selectively moveable with respect to said adjustable frame and having first and second ends, wherein said extension device further comprises a positioning arm adjustably coupled to said frame and having first and second ends, wherein said first end is adapted for mounting to said adjustable frame, and said second end is adapted for mounting to a tool holder, wherein said adjustable frame includes two frame members each having first and second spaced apart ends, said first ends of said frame members being mechanically coupled for varying, a spatial proximity between said second ends of said frame members, wherein at least one of said frame members includes first mounting means for said removable and replaceable mounting of said first end of said positioning arm to said adjustable frame, and wherein said first mounting means further includes an aperture in said at least one frame, and said surgical retractor further includes a clamp assembly adapted for slidable and lockable attachment to said aperture and for removable and replaceable coupling said first end of said positioning arm to said frame member.

* * * * *